United States Patent [19]
Bös et al.

[11] Patent Number: 5,998,665
[45] Date of Patent: Dec. 7, 1999

[54] USE OF SULFONAMIDES

[75] Inventors: Michael Bös, Rheinfelden, Switzerland; Claus Riemer, Freiburg, Germany; Andrew Sleight, Riedisheim, France

[73] Assignee: Hoffmann-La Roche Inc., Nutley, N.J.

[21] Appl. No.: 09/089,706

[22] Filed: Jun. 3, 1998

Related U.S. Application Data

[62] Division of application No. 08/869,063, Jun. 4, 1997.

[51] Int. Cl.$^6$ .......................... C07C 311/21; A61K 31/63
[52] U.S. Cl. ........................... 564/86; 514/603; 514/604; 514/92
[58] Field of Search ...................... 564/86, 92; 514/603, 514/604

[56] References Cited

U.S. PATENT DOCUMENTS

| | | | |
|---|---|---|---|
| 2,192,490 | 3/1940 | Warnat | 260/556 |
| 3,328,395 | 6/1967 | Nitta et al. | 260/239.75 |
| 5,130,119 | 7/1992 | Blaszkiewicz et al. | 424/9 |

FOREIGN PATENT DOCUMENTS

| | | |
|---|---|---|
| 1383287 | 12/1963 | France . |
| 202173 | 7/1992 | Japan . |
| WO 92/14456 | 9/1992 | WIPO . |

OTHER PUBLICATIONS

Chio, L. et al. Antimicrobiol. Agents and Chemotherapy, Mar. 1996, pp. 727–733.
Bryan L. Roth et al., J. Pharmacol. Exp. Ther. 268, pp. 1403–1410 (1994).
David R. Sibley et al., Mol. Pharmacol. 43, pp. 320–327 (1993).
Anne Bourson et al., J. Pharmacol. Exp. Ther. 274 pp. 173–180 (1995).
R.P. Ward, et al. Neuroscience, 64, pp. 1105–1110 (1995).
Andrew J. Sleight et al. Neurotransmissions 11, pp. 1–5 (1995).
R. Behnisch et al., Chemische Berichte, 81, No. 4, pp. 297–306 (1947).
J.L. Federick et al., Journal of Org. Chem. 26, pp. 4715–4716 (1961).
J.K. Seydel, Mol. Pharmacol. 2, pp. 259–265 (1966).
Bergeim et al., Journal of the American Chem. Soc. 69, pp. 583–587 (1947).
R. Urban et al., Helvetica Chimica Acta 47, pp. 363–379 (1964).
Bretschneider et al., Monatshefte für Chemie, 92, pp. 183–192 (1961).
Bretschneider et al., Monatshefte für Chemie, 95, pp. 207–213 (1963).
W. Baker et al. Journal of the Am. Chem. Soc. 69, pp. 3072–3078 (1947).

*Primary Examiner*—Evelyn Mei Huang
*Attorney, Agent, or Firm*—George W. Johnston; Patricia S. Rocha-Tramaloni; Robert A. Silverman

[57] ABSTRACT

The present invention is concerned with compounds of formula I

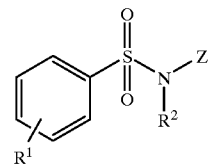

wherein Z, $R^1$ and $R^2$ are as defined herein, as well as their pharmaceutically acceptable salts as therapeutically active substances against central nervous system disorders and for the production of corresponding medicaments.

10 Claims, No Drawings

USE OF SULFONAMIDES

This is a divisional of copending application Ser. No. 08/869,063 filed on Jun. 4, 1997.

SUMMARY OF THE INVENTION

The invention is concerned with compounds of formula

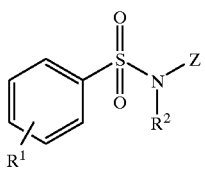

I wherein

Z is a substituted phenyl, substituted pyridyl, substituted pyrimidyl or substituted indolyl group of formula a–e

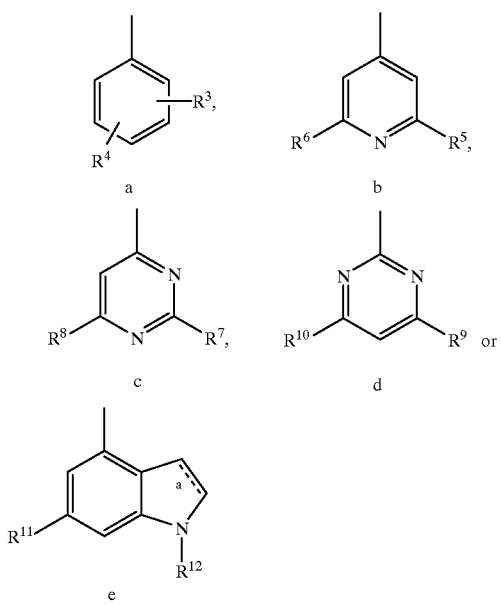

$R^1$ is hydrogen, amino, lower alkylamino, lower dialkylamino, lower alkyl, halogen or trifluoromethyl;

$R^2$ is hydrogen or lower alkyl;

$R^3$ is hydrogen, amino, lower alkylamino, lower dialkylamino, lower alkyl, $CF_3$, lower alkoxy or halogen;

$R^4$ is amino, lower alkylamino, lower dialkylamino, lower alkyl, lower alkoxy or halogen;

$R^5$ is hydrogen, lower alkyl, lower alkylamino, di-lower alkylamino, lower alkoxy or halogen;

$R^6$ is lower alkylamino, di-lower alkylamino, lower alkoxy, halogen or $CF_3$;

$R^7$ is amino, lower alkylamino, di-lower alkylamino, lower alkoxy, lower alkylsulfanyl, mercapto, pyrrolidin-1-yl or azetidin-1-yl;

$R^8$ is amino, lower alkylamino, di-lower alkylamino, benzylamino, lower alkoxy, lower alkylsulfanyl, halogen, pyrrolidin-1-yl or azetidin-1-yl;

$R^9$ and $R^{10}$ each independently are lower alkoxy or lower alkylamino;

$R^{11}$ is hydrogen or halogen;

$R^{12}$ is hydrogen or lower alkyl, and a is an optional double bond, with the proviso that $R^7$ and $R^8$ do not simultaneously signify methoxy, as well as their pharmaceutically acceptable salts, and their administration to a host in need for use as therapeutically active substances.

It has been found that the compounds of formula I, as well as their pharmaceutically acceptable salts, surprisingly possess a selective affinity to 5HT-6 receptors. They are accordingly useful for the treatment or prevention of Alzheimer's Disease. They are also useful for the treatment or prevention of central nervous disorders such as, for example, psychoses, schizophrenia, manic depressions (Bryan L. Roth et al., J. Pharmacol. Exp. Ther., 268, pages 1403–1410 (1994)), depressions (David R. Sibley et al., Mol. Pharmacol., 43, pages 320–327 (1993)), neurological disorders (Anne Bourson et al., J. Pharmacol. Exp. Ther., 274, pages 173–180 (1995); R. P. Ward et al., Neuroscience, 64, pages 1105–1110 (1995)), memory disorders, Parkinson's disease, amyotrophic lateral sclerosis and Huntington's disease (Andrew J. Sleight et al., Neurotransmissions, 11, pages 1–5 (1995)).

An object of the present invention is the use of compounds of formula I and of their pharmaceutically usable salts for the treatment or prevention of illnesses of the aforementioned kind and, respectively, for the production of corresponding medicaments, the compounds of formulas $Ia_1$, $Ia_2$, $Ib_1$, $Ib_2$, $Ic_1$, $Ic_2$, $Id_1$, $Id_2$ and Ie or their pharmaceutically usable salt per se or for use as therapeutically active substances, the manufacture of the compounds of formulas $Ia_1$, $Ia_2$, $Ib_1$, $Ib_2$, $Ic_1$, $Ic_2$, $Id_1$, $Id_2$ and Ie, medicaments containing a compound of formula I or pharmaceutically usable salt thereof as well as the production of such medicaments.

DETAILED DESCRIPTION OF THE INVENTION

Known compounds of formula I in which Z is a substituted phenyl residue are described for example by R. Behnisch et al. in Chemische Berichte, 81, No. 4, pages 297–306, (1947), for example compounds with halogen substituents on the phenyl residue such as 4-amino-N-(3,5-dichlorophenyl)-benzenesulfonamide or 4-amino-(3,5-dibromo-phenyl)-benzenesulfonamide, or compounds with methyl or methoxy substituents on the phenyl residue such as 4-amino-N-(3,5-dimethyl-phenyl)-benzenesulfonamide or 4-amino-N-(3,5-dimethoxy-phenyl)-benzenesulfonamide. The sulfonamides described here have an activity against malaria.

J. L. Frederick et al. in Journal of Org. Chem., 26, pages 4715–4716, (1961) describe fluorosulfanilanilides such as, for example, the compound 4-amino-N-(3,5-difluorophenyl)-benzenesulfonamide, as well as their production and use as antibacterial agents.

Further, J. K. Seydel in Mol. Pharmacol., 2, pages 259–265, (1966) describes the in vitro activity of a series of sulfonamides against *E coli*.

Bergeim et al. in Journal of the American Chem. Soc., 69, pages 583–587, (1947) describe the production of some amino-sulfanilanisides such as, for example, the compound 4-amino-N-(3-methoxy-phenyl)-benzenesulfonamide as possible antimalarial agents.

Not one of the publications enumerated above mentions that phenyl-benzenesulfonamides could also suitable as active compounds for the treatment of neurological disorders.

Known compounds of formula I in which Z is a substituted pyridine residue are described, for example, by R.

Urban et al. in Helvetia Chimica Acta, 47, pages 363–377, (1964), for example the compounds 4-amino-N-(4,6-dimethoxy-pyridin-2-yl)-benzenesulfonamide, 4-amino-N-(2-methoxy-6-bromo-pyridin-3-yl)-benzenesulfonamide, 4-amino-N-(2-methoxy-6-methyl-pyridin-4-yl)-benzenesulfonamide or 4-amino-N-(2,6-dimethoxy-pyridin-4-yl)-benzenesulfonamide. The production of aminomethoxypyridines and sulfanilamides is described, together with their antibacterial properties. Also in this publication no mention is to be found with respect to a potential activity against neurological disorders.

Known compounds of formula I in which Z is a substituted pyrimidine residue are described for example by Bretschneider et al. in Monatshefte für Chemie, 92, pages 183–192, (1961). The production of 2,6-disubstituted 4-sulfanilamidopyrimidines, for example of the compound 4-amino-N-(2,6-diethylsulfanyl-pyrimidin-4-yl)-benzenesulfonamide, is described. In Monatshefte für Chemie, 95, pages 207–213, (1964) Bretschneider et al. describe further syntheses of 6-sulfanilamido-2,4-dimethoxypyrimidine.

W. Baker et al. in Journal of the American Chem. Soc., 69, pages 3072–3078, (1947) describe the production of substituted sulfanilamidopyrimidines, such as, for example, the compound 4-amino-N-(4,6-dimethoxy-pyrimidin-2-yl)-benzenesulfonamide, as well as their potential use as antibacterial agents.

Sulfanil derivatives of 2,6-di-substituted pyrimidines, such as, for example, the compound 4-amino-N-(2,6-bis-dimethylamino-pyrimidin-4-yl)-benzenesulfonamide, are described in French Patent Application FR 1 383 287.

Not one of these publications mentions that sulfonamides which carry a pyrimidine residue could also be suitable as an active compounds for the treatment of neurological disorders.

The use of compounds which carry a primary amino group for the treatment of neurological disorders is quite generally described in International Patent Application WO 92/14456. A large number of different groups of compound, such as, for example, p-aminobenzoic acids, p-aminophenylacetic acids, aminonicotinic acid, 2,3-diamino-propionic acid and the like are named. In this enumeration of different groups of compound there are also named, inter alia, sulfanilamides and 1-amino substituted derivatives of sulfanilamides (p-H$_2$N-C$_6$H$_4$-SO$_2$NHR). The compound 4-amino-N-(2,6-dimethoxy-pyrimidin-4-yl)-benzenesulfonamide specifically referred to by name is excluded by means of a disclaimer from the use of the compounds of formula I for the treatment or prevention of disorders of the aforementioned kind.

The compounds of formula I embrace the following groups:

a) anilides of formula Ia

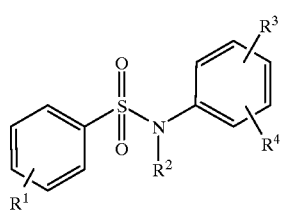

Ia wherein $R^1$, $R^2$, $R^3$ and $R^4$ have the significances given in formula I;

b) compounds of formula Ib

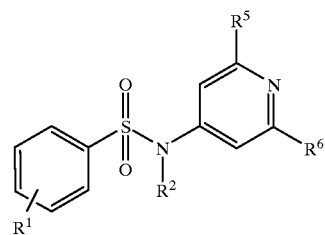

Ib wherein $R^1$, $R^2$, $R^5$ and $R^6$ have the significances given in formula I;

c) compounds of formulae Ic and Id

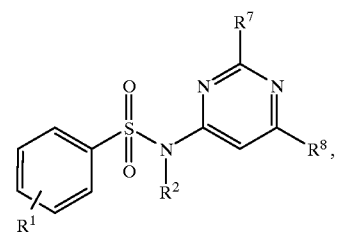

Ic

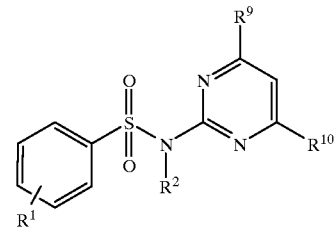

Id wherein $R^1$, $R^2$, $R^7$, $R^8$, $R^9$ and $R^{10}$ have the significances given in formula I;

and d) compounds of formula Ie

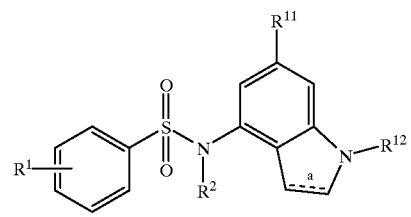

Ie wherein $R^1$, $R^2$, $R^{11}$, $R^{12}$ and a have the significances given in formula I.

The following compounds of formulae Ia, Ib, Ic, Id and Ie are especially preferred for a use of the aforementioned kind:

4-Amino-N-(2,6-bis-methylamino-pyrimidin-4-yl)-benzenesulfonamide;

4-amino-N-(6-ethylamino-2-methylamino-pyrimidin-4-yl)-benzenesulfonamide;

4-amino-N-(2-dimethylamino-6-methylamino-pyrimidin-4-yl)-benzenesulfonamide;

4-amino-N-(2-dimethylamino-6-ethylamino-pyrimidin-4-yl)-benzenesulfonamide;

4-amino-N-(2,6-bis-methylamino-pyrimidin-4-yl)-N-methyl-benzenesulfonamide;

4-amino-N-(2-azetidin-1-yl-6-methylamino-pyrimidin-4-yl)-benzenesulfonamide;

4-amino-N-(2-azetidin-1-yl-6-ethylamino-pyrimidin-4-yl)-benzenesulfonamide;

4-amino-N-(6-methylamino-2-pyrrolidin-1-yl-pyrimidin-4-yl)-benzenesulfonamide;

4-amino-N-(2-bromo-6-methylamino-pyridin-4-yl)-benzenesulfonamide;

4-amino-N-(2,6-bis-methylamino-pyridin-4-yl)-benzenesulfonamide;

4-amino-N-(2-ethylamino-6-methylamino-pyridin-4-yl)-benzenesulfonamide;

4-amino-N-(2-dimethylamino-6-methylamino-pyridin-4-yl)-benzenesulfonamide;

4-amino-N-(2,6-bis-ethylamino-pyridin-4-yl)-benzenesulfonamide;

N-(2,6-bis-methylamino-pyrimidin-4-yl)-3-chloro-benzenesulfonamide;

N-(2,6-bis-methylamino-pyrimidin-4-yl)-3-trifluoromethyl-benzenesulfonamide;

4-amino-N-(2-methyl-6-methylamino-pyridin-4-yl)-benzenesulfonamide;

4-amino-N-(3,5-dimethoxy-phenyl)-benzenesulfonamide;

4-amino-N-(3,5-dichloro-phenyl)-benzenesulfonamide;

4-amino-N-(3,5-dibromo-phenyl)-benzenesulfonamide and 4-amino-N-(1H-indol-4-yl)-benzenesulfonamide.

The term "lower alkyl" used in the present description denotes residues of 1 to 7, preferably of 1 to 4, carbon atoms, such as, for example, methyl, ethyl, n-propyl, i-propyl, n-butyl, i-butyl and t-butyl.

The term "lower alkoxy" denotes a lower alkyl residue in the sense of the foregoing definition bonded via an oxygen atom, such as, for example, methoxy, ethoxy, n-propoxy, i-propoxy, n-butoxy, i-butoxy and t-butoxy.

The term "lower alkylamino" denotes a lower alkyl residue in the sense of the foregoing definition bonded via a NH group, such as, for example, methylamino and ethylamino.

The term "lower dialkylamino or di-lower alkylamino" denotes two similar or different lower alkyl residues in the sense of the foregoing definition bonded via a nitrogen atom, such as, for example, dimethylamino, diethylamino or methyl-ethyl-amino.

The term "lower alkylsulfanyl" denotes a lower alkyl residue in the sense of the foregoing definition bonded via a sulfur atom, such as, for example, methylsulfanyl (—S—$CH_3$) and ethylsulfanyl (—S—$CH_2CH_3$).

The term "halogen" embraces fluorine, chlorine, bromine and iodine.

With respect to formula Ia, the following known compounds are preferred or especially preferred for use as therapeutically active substances:

4-Amino-N-(3,5-dimethoxy-phenyl)-benzenesulfonamide, 4-amino-N-(3,5-dichloro-phenyl)-benzenesulfonamide, 4-amino-N-(3,5-dibromo-phenyl)-benzenesulfonamide, 4-amino-N-(3,5-dimethyl-phenyl)-benzenesulfonamide and 4-amino-N-(3-methoxy-phenyl)-benzenesulfonamide.

In one aspect, the invention relates to compounds of formulas $Ia_1$ and $Ia_2$

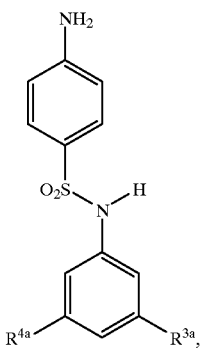

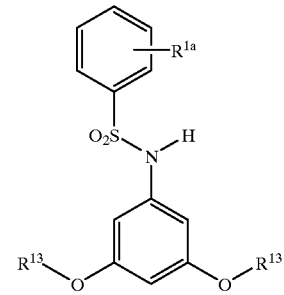

wherein $R^{1a}$ signifies 3-trifluoromethyl, 3-halo or 4-halo;

$R^{3a}$ signifies hydrogen, halogen, lower alkoxy, amino or lower alkylamino;

$R^{4a}$ signifies amino or lower alkylamino and $R^{13}$ signifies lower alkyl;

with the proviso that $R^{3a}$ is different from hydrogen when $R^{4a}$ signifies amino, as well as their pharmaceutically acceptable salts.

Preferred compounds of formula $Ia_1$ in which $R^{3a}$ signifies hydrogen, amino or methylamino and $R^{4a}$ signifies amino or methylamino and their manufacture are described in Examples 34–36.

Example 37 describes the manufacture of a compound of formula $Ia_2$ in which $R^{1a}$ signifies 3-trifluoromethyl and $R^{13}$ signifies methyl.

With respect to formula Ib, the following known compounds are preferred for use as therapeutically active substances:

4-Amino-N-(2,6-dimethoxy-pyridin-4-yl)-benzenesulfonamide and 4-amino-N-(2-methoxy-6-methyl-pyridin-4-yl)-benzenesulfonamide.

In one aspect, the invention relates to compounds of formulas $Ib_1$ and $Ib_2$

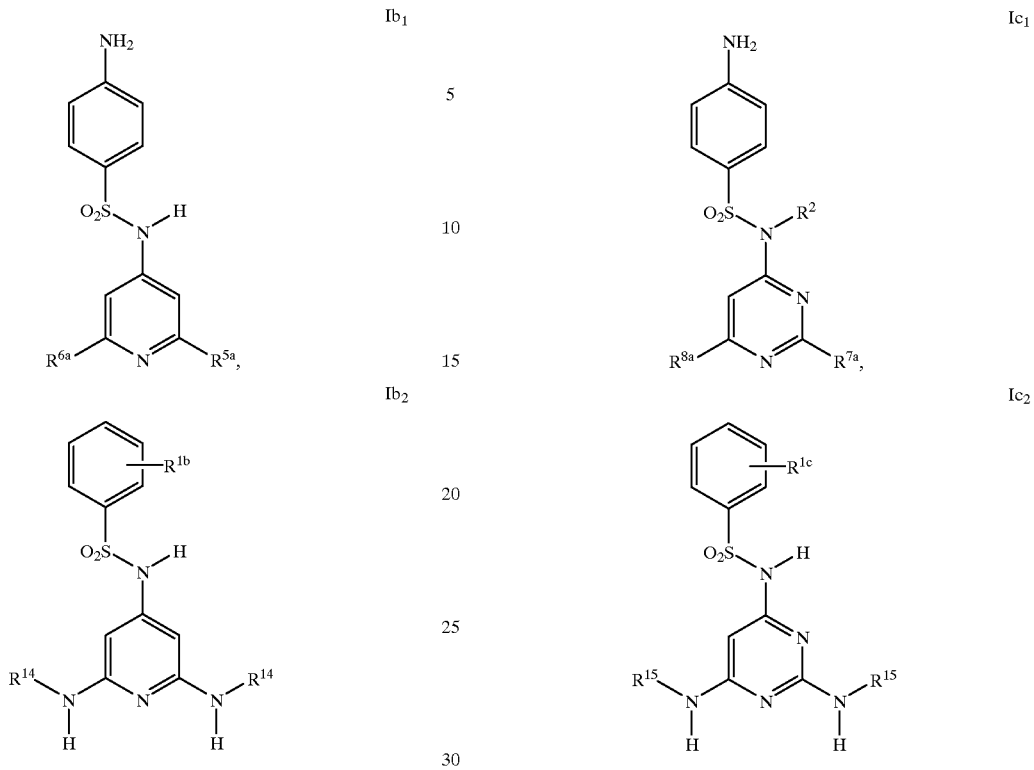

wherein

R$^{1b}$ signifies 4-halo, 3-halo or 3-trifluoromethyl;

R$^{5a}$ signifies hydrogen, lower alkyl, lower alkylamino, di-lower alkylamino or halogen;

R$^{6a}$ signifies CF$_3$, lower alkylamino, di-lower alkylamino or halogen and

R$^{14}$ signifies lower alkyl;

with the proviso that R$^{5a}$ is different from hydrogen when R$^{6a}$ signifies halogen, as well as their pharmaceutically acceptable salts.

Preferred are compounds of formula Ib$_1$ in which

R$^{5a}$ signifies hydrogen, methyl, methylamino, ethylamino, dimethylamino, chlorine or bromine and R$^{6a}$ signifies methylamino, ethylamino, dimethylamino, CF$_3$ or bromine, with the proviso that R$^{5a}$ is different from hydrogen when R$^{6a}$ signifies bromine, and their manufacture are described in Examples 38–47, 51 and 53.

Preferred compounds of formula Ib$_2$ in which

R$^{1b}$ signifies 4-chloro, 3-chloro or 3-trifluoromethyl and

R$^{14}$ signifies methyl, and their manufacture are described in Examples 48–50.

In one aspect, the invention relates to compounds of formulas Ic$_1$ and Ic$_2$ wherein R$^{1c}$ signifies hydrogen, 4-halo, 4-lower alkyl, 3-halo or 3-trifluoromethyl;

R$^2$ signifies hydrogen or lower alkyl;

R$^{7a}$ signifies amino, lower alkylamino, di-lower alkylamino, mercapto, pyrrolidin-1-yl or azetidin-1-yl;

R$^{8a}$ signifies amino, lower alkylamino, di-lower alkylamino, benzylamino, lower alkoxy, pyrrolidin-1-yl or azetidin-1-yl and R$^{15}$ signifies lower alkyl;

with the proviso that R$^{8a}$ is different from lower alkoxy and from di-lower alkylamino when R$^{7a}$ signifies di-lower alkylamino, as well as their pharmaceutically acceptable salts.

In one aspect, the invention relates to compounds of formula Ic$_1$ in which

R$^2$ signifies hydrogen or methyl;

R$^{7a}$ signifies amino, methylamino, ethylamino, propylamino, isopropylamino, dimethylamino, mercapto, pyrrolidin-1-yl or azetidin-1-yl and R$^{8a}$ signifies amino, methylamino, ethylamino, propylamino, isopropylamino, dimethylamino, benzylamino, methoxy, pyrrolidin-1-yl or azetidin-1-yl, with the proviso that R$^{8a}$ is different from dimethylamino and methoxy when R$^{7a}$ signifies dimethylamino, and their manufacture are described in Examples 1–25.

In one aspect, the invention relates to compounds of formula Ic$_2$ in which

R$^{1c}$ signifies hydrogen, 4-fluoro, 4-chloro, 4-methyl, 4-tert.butyl, 3-chloro or 3-trifluoromethyl and R$^{15}$ signifies methyl, and their manufacture are described in Examples 27–33.

In one aspect, the invention relates to compounds of formulas Id$_1$ and Id$_2$

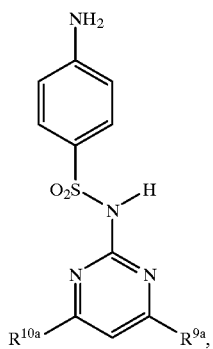

Id₁

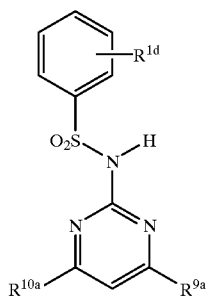

Id₂ wherein $R^{1d}$ signifies 3-trifluoromethyl, 4-trifluoromethyl, 3-halo or 4-halo and $R^{9a}$ and $R^{10a}$ signify lower alkylamino, as well as their pharmaceutically acceptable salts.

Example 26 describes the manufacture of a compound of formula Id₁ in which $R^{9a}$ and $R^{10a}$ signify methylamino.

In one aspect, the invention relates to compounds of formula Ie

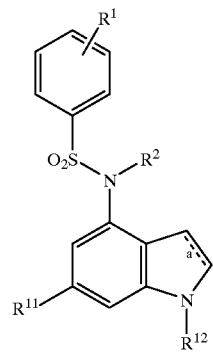

Ie wherein $R^1, R^2, R^{11}, R^{12}$ and a have the significance given in claim 1.

The manufacture of compounds of formula Ie in which $R^1$ is amino and $R^{11}$ is hydrogen is described in Example 52.

The compounds of formula I and their salts, insofar as they are one aspect of the invention and their manufacture has not already been described, can be manufactured in a known manner from a compound of formula II

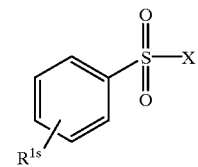

II wherein $R^{1s}$ has the significance given for $R^1$ or signifies protected amino and X signifies halogen or —NHY in which Y stands for an alkali metal, for example sodium or potassium, by reacting a compound of formula II in which X signifies halogen:

a) with a compound of the formula

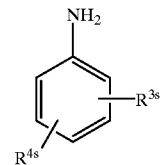

IIIa wherein $R^{3s}$ signifies hydrogen, lower alkoxy, halogen, protected amino or protected lower alkylamino and $R^{4a}$ signifies protected amino or protected lower alkylamino, and cleaving of the amino protecting groups; or b) with a compound of the formula

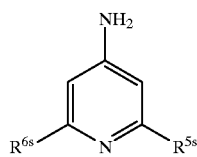

IIIb wherein $R^{5s}$ signifies halogen and $R^{6s}$ signifies halogen, lower alkyl or $CF_3$, and, if desired, reacting the reaction product with a lower alkylamine or di-lower alkylamine and cleaving off the amino protecting group; or c) with a compound of the formula

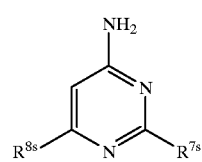

IIIc wherein $R^{7s}$ signifies mercapto and $R^{8s}$ signifies amino, lower alkylamino, di-lower alkylamino, benzylamino, lower alkoxy, pyrrolidin-1-yl or azetidin-1-yl, and, if necessary, cleaving off the amino protecting group; or d) reacting a compound of formula II in which X signifies —NHY firstly with a compound of the formula

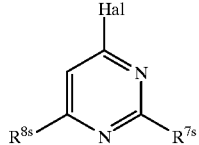

IIId wherein $R^{7s}$ signifies amino, lower alkylamino, mercapto, pyrrolidin-1-yl or azetidin-1-yl and $R^{8s}$ signifies halogen, and then, if desired, treating the reaction product with a lower alkylamine, di-lower alkylamine, azetidine, pyrrolidine or an alcoholate; or e) reacting a compound of formula II in which X signifies halogen with a compound of the formula

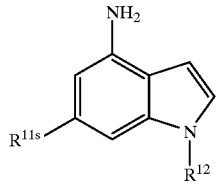

IIIe wherein $R^{11s}$ signifies hydrogen or halogen and $R^{12}$ signifies hydrogen or lower alkyl, and, if desired, reducing to a compound of formula Ie in which a does not signify a double bond; or f) reacting a compound of the formula

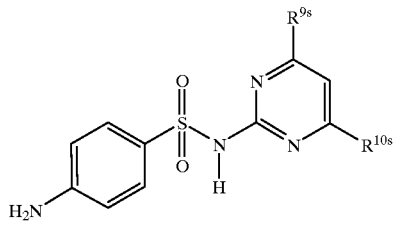

IV wherein $R^{9s}$ and $R^{10s}$ signify lower alkoxy, with a lower alkylamine; or g) reacting a sulfadimethoxine of the formula

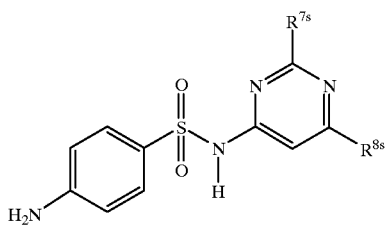

V wherein $R^{7s}$ and $R^{8s}$ signify lower alkoxy, with a lower alkylamine; and h) if desired, converting a compound of formula I into a pharmaceutically acceptable salt.

All process variants referred to herein can be carried out in a known manner.

For the manufacture of compounds of formula Ia, the starting materials of formulae II and IIIa are conveniently reacted at room temperature in a suitable solvent, for example pyridine.

For the alkylation of the amino group, the protected amino group can be reacted, for example, with a lower alkyl iodide.

The acetyl group is a suitable amino protecting group.

The cleavage of the amino protecting group is effected by the addition of a base (e.g. NaOH) by heating under reflux.

In the case of compounds of formula Ia the protecting group cleavage is always the last reaction step.

For the manufacture of compounds of formula Ib, the starting materials of formula II (X=halogen) and IIIb are conveniently reacted at 20–80° C., preferably at 60° C., in a suitable solvent, for example pyridine.

For the manufacture of compounds of formula Ic, the starting materials of formula II (X=halogen) are reacted with compounds of formula IIIc.

The cleavage of the amino protecting group is effected by base treatment as described above.

The reaction product of the reaction of a compound of formula II with a compound of formula IIIb, for example 4-amino-N-(2,6-dibromo-pyridin-4-yl)-benzenesulfonamide, can be used for the manufacture of compounds of formula Ib in which $R^5$ signifies halogen, lower alkylamino or di-lower alkylamino and $R^6$ represents lower alkylamino or di-lower alkylamino by reaction with a lower alkylamine or di-lower alkylamine at 60–200° C.

For the manufacture of compounds of formula I in which $R^2$ signifies lower alkyl, a corresponding sulfonamide can be reacted with diazomethane in a known manner (Example 19).

The starting materials required for the manufacture of the compounds of formula I are known compounds or can be prepared in analogy to known processes. These reactions will be familiar to any person skilled in the art.

The binding of the compounds of formula I in accordance with the invention to 5-HT$_6$ receptors was determined as follows.

Membranes obtained from HEK 293 cells which had been transfected with 5-HT$_6$ receptors from rats were used.

The cells were purified by two-fold centrifugation (10 minutes at 3000 g) in phosphate-buffered sodium chloride solution. The cell mass was suspended in an ice-cold solution consisting of 50 mM Tris-HCl buffer, 10 mM MgCl$_2$, 0.5 mM EDTA and 0.1 mM phenylmethylsulfonyl fluoride and homogenized (Polytron homogenizer, 15 seconds at maximum velocity). The homogenizate was incubated at 37° C. for 10 minutes and subsequently centrifuged (20 minutes at 20,000 g). The cell mass was again suspended in the aforementioned Tris buffer solution. The resulting cell concentration was $4 \times 10^7$ cells/ml. Aliquots each comprising 1 ml of the homogenizate were freeze-dried at $(-80)°$ C.

Displacement tests were carried out in order to determine the affinity of the test substance to the $5\text{-HT}_6$ receptor. In order to carry out the test, the homogenizate was thawed and suspended in a buffer solution (pH 7.4) consisting of 50 mM Tris-HCl buffer, 5 mM $MgCl_2$, $10^{-5}M$ pargyline and 0.1% ascorbic acid. 100 µl of membrane suspension, 50 µl of [$^3$H]-LSD (specific activity 85 Ci/Mmol, final concentration 1nM) and 50 µl of test substance solution were incubated at 37° C. for 1 hour. The respective substance was investigated at 7 different concentrations from $10^{-10}M$ to $10^{-4}M$. The binding reaction of the test substance was interrupted by rapid filtration through [a] Whatman GF/B filter. The filter was washed with 2×2 ml of Tris-HCl buffer (50 mM, pH 7.4) and the radioactivity on the filter was measured by scintillation spectroscopy in 2 ml of scintillation solution. All tests were carried out in triplicate and were repeated three times.

The pKi values (pKi=$-\log_{10}$Ki) of the test substances have been determined. The Ki value is defined by the following formula:

$$Ki = \frac{IC_{50}}{1 + \frac{[L]}{K_D}}$$

with the $IC_{50}$ values being those concentrations of test compounds in nM by which 50% of the ligands bonded to the receptor are displaced. [L] is the concentration of ligand and the $K_D$ value is the dissociation constant of the ligand.

The compounds in accordance with the invention have a selective affinity to 5-HT 6 receptors with a Ki value below 1.6 µM and pKi values between 6.00 and 8.00.

The compounds of formula I and the pharmaceutically acceptable salts of the compounds of formula I can be used as medicaments, for example in the form of pharmaceutical preparations. The pharmaceutical preparations can be administered orally, for example in the form of tablets, coated tablets, dragees, hard and soft gelatine capsules, solutions, emulsions or suspensions. The administration can, however, also be effected rectally, for example in the form of suppositories, parenterally, for example in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises by bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful for treating or preventing Alzheimer's Disease. The compounds of formula I and their pharmaceutically acceptable salts are also useful in the treatment or prevention of central nervous disorders such as depressions, psychoses, schizophrenia, neurological disorders, memory disorders, Parkinson's disease, amoytrophic lateral sclerosis and Huntington's disease and for the production of corresponding medicaments. The dosage can vary within wide limits and will, of course, be fitted to the individual requirements in each particular case. In the case of oral administration the dosage lies in range of about 0.01 mg per dose to about 1,000 mg per day of a compound of general formula I or the corresponding amount of a pharmaceutically acceptable salt thereof, although the upper limit can also be exceeded when this is found to be indicated.

The following Examples illustrate the present invention in more detail. However, they are not intended to limit its scope in any manner.

EXAMPLE 1

4-Amino-N-(2-amino-6-methylamino-pyrimidin-4-yl)-benzenesulfonamide 0.98 g (0.006 mol) of 2-amino-4,6-dichloropyrimidine and 3.03 g (0.012 mol) of N-(4-sulfamoyl-phenyl)-acetamide potassium salt were stirred in 10 ml of 1-methyl-2-pyrrolidone at 140° C. for 8 hours. Then, the solvent was distilled off in a high vacuum, the residue was partitioned in ethyl acetate/water, the inorganic phase was saturated with sodium chloride and the remaining ethyl acetate dissolved in the aqueous was distilled off on a rotary evaporator. The aqueous phase was made acid with 1N HCl, the crystals which separated were filtered off under section and washed with water. After drying there were obtained 1.37 g (67%) of N-[4-(2-amino-6-chloro-pyrimidin-4-ylsulfamoyl)-phenyl]-acetamide as beige crystals; m.p.: 272–273° C. (dec.).

0.885 g (0.0026 mol) of N-[4-(2-amino-6-chloropyrimidin-4-ylsulfamoyl)phenyl]-acetamide was dissolved in 31 ml of 0.5N NaOH and boiled at reflux for 3 hours. The mixture was extracted with ethyl acetate, the aqueous phase was saturated with sodium chloride and the remaining ethyl acetate was distilled off on a rotary evaporator. Then, the aqueous phase was made acid with 3N HCl and the precipitate which separated was filtered off under suction.

After drying there was obtained 0.76 g (86%) of 4-amino-N-(2-amino-6-chloro-pyrimidine-4-yl)-benzenesulfonamide as beige crystals; m.p.: >265° C. (dec.).

0.527 g (0.00176 mol) of 4-amino-N-2-amino-6-chloro-pyrimidin-4-yl)benzenesulfonamide was dissolved in 22 ml (0.176 mol) of 8M methylamine in ethanol and stirred in an autoclave at 130° C. for 16 hours. The suspension obtained was filtered, the precipitate was dissolved in ethanol and treated with active charcoal, filtered and freed from the solvent. The residue was suspended in ethanol and filtered. There was obtained 0.055 g (10%) of 4-amino-N-(2-amino-6-methylamino-pyrimidin-4-yl)-benzenesulfonamide as beige crystals; m.p.: 285° C. (dec.).

EXAMPLE 2
4-Amino-N-(2-amino-6-ethylamino-pyrimidin-4-yl)-benzenesufonamide 0.50 g (0.00167 mol) of 4-amino-N-(2-amino-6-chloro-pyrimidin-4-yl)-benzenesufonamide and 11 ml (0.167 mol) of ethylamine were dissolved in 20 ml of ethanol and stirred in an autoclave at 130° C. for 4 hours. The reaction mixture was freed from solvent, the residue was suspended in 5 ml of ethanol and treated in an ultrasound bath for 15 minutes. The precipitate was filtered off, dissolved 10 ml of 0.1N NaOH and filtered. The filtrate was adjusted to pH 6 with 0.1N HCl. The precipitate was filtered off under suction, washed with water and dried. There was obtained 0.271 g (53%) of 4-amino-N-(2-amino-6-ethylamino-pyrimidin-4-yl)-benzenesulfonamide as beige crystals; m.p. 272–274° C.

EXAMPLE 3
4-Amino-N-(2-amino-6-benzylamino-pyrimidin-4-yl)-benzenesulfonamide 0.30 g (0.001 mol) of 4-amino-N-(2-amino-6-chloro-pyrimidin-4-yl)-benzenesulfonamide and 11 ml (0.1 mol) of benzylamine were dissolved in 15 ml of ethanol and stirred in an autoclave at 130° C. The reaction mixture was freed from solvent, the residue was suspended in 5 ml of ethanol and treated in an ultrasound bath for 15 minutes. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.15 g (41%) of 4-amino-N-(2-amino-6-benzylamino-pyrimidin-4-yl)-benzenesulfonamide as beige crystals; m.p.; 221° C. (dec.).

EXAMPLE 4
4-Amino-N-(2,6-bis-methylamino-pyrimidin-4-yl)-benzenesulfonamide 5.0 g (0.016 mol) of sulfadimethoxine were dissolved in 60 ml of 33 percent ethanolic methylamine and stirred in an autoclave at 150° C. for 30 hours. The mixture was cooled, freed completely from solvent, triturated in 70 ml of methanol for 2 hours. and suction filtered. There were obtained 4.2 g (84%) of 4-amino-N-(2,6-bis-methylamino-pyrimidin-4-yl)-benzenesulfonamide as grey crystals; m.p. 303–305° C.

11.5 g (0.0373 mol) of 4-amino-N-(2,6-bis-methylamino-pyrimidin-4-yl)-benzenesulfonamide were treated with 11.5 ml of 25 percent aqueous hydrochloric acid and stirred at 0° C. for 1 hour. The water was evaporated completely and the residue was recrystallized from ethanol/diethyl ether. There were obtained 11.8 g (89%) of 4-amino-N-(2,6-bis-methylamino-pyrimidin-4-yl)-benzenesulfonamide hydrochloride (1:1.8) as pale yellow crystals; m.p. 175–250° C. (dec.).

EXAMPLE 5
4-Amino-N-(6-ethylamino-2-methylamino-pyrimidin-4-yl) benzenesulfonamide 2.0 g (0.011 mol) of (4,6-dichlorpyrimidin-2-yl)-methylamine and 5.67 g (0.022 mol) N-(4-sulfamoyl-phenyl)-acetamide potassium salt were stirred in 10 ml of 1-methyl-2-pyrrolidone at 140° C. for 8 hours. Then, the solvent was distilled off in a high vacuum, the residue was partitioned in ethyl acetate/water, the inorganic phase was saturated with sodium chloride and the residual ethyl acetate dissolved in the aqueous phase was distilled off on a rotary evaporator. The aqueous phase was made acid with 1N HCl, the crystals which separated were filtered off under suction and washed with water. After drying there were obtained 2.72 g (68%) of N-[4-(6-chloro-2-methylamino-pyrimidin-4-ylsulfamoyl)-phenyl]-acetamide as beige crystals. m.p.: >240° C. (dec.).

2.7 g (0.008 mol) of N-[4-(6-chloro-2-methylamino-pyrimidin-4-ylsulfamoyl)-phenyl]-acetamide were dissolved in 76 ml of 1N NaOH and boiled at reflux for 3 hours. The mixture was extracted with ethyl acetate, the aqueous phase was saturated with sodium chloride and the residual ethyl acetate was distilled off on a rotary evaporator. Then, the aqueous phase was made acid with 3N HCl and the precipitate which separated was filtered off under suction. After drying there were obtained 2.12 g (89%) of 4-amino-N-(6-chloro-2-methylamino-pyrimidin-4-yl)-benzenesulfonamide hydrochloride (1:1.9) as white crystals; MS (ISN): me/e=312 ($C_{11}H_{11}ClN_5O_2S^-$).

0.314 g (0.001 mol) of 4-amino-N-(6-chloro-2-methylamino-pyrimidin-4-yl)-benzenesulfonamide and 6.6 ml (0.1 mol) of ethylamine were stirred in 15 ml of ethanol in an autoclave at 130° C. for 3 hours. The reaction mixture was freed from solvent, the residue was suspended in 8 ml of ethanol and treated in an ultrasound bath for 15 minutes. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.18 g (56%) of 4-amino-N-(6-ethylamino-2-methylamino-pyrimidin-4-yl)-benzenesulfonamide as white crystals; m.p.: 252° C. (dec.).

EXAMPLE 6
4-Amino-N-(6-isopropylamino-2-methylamino-pyrimidin-4-yl)-benzenesulfonamide 0.314 g (0.001 mol) of 4-amino-N-(6-chloro-2-methylamino-pyrimidin-4-yl)-benzenesulfonamide and 8.6 ml (0.1 mol) of isopropylamine were stirred in 15 ml of ethanol in an autoclave at 130° C. for 3 hours. The reaction mixture was freed from solvent, the residue was suspended in 8 ml of ethanol and treated in an ultra sound bath for 15 minutes. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.12 g (36%) of 4-amino-N-(6-isopropylamino-2-methylamino-pyrimidin-4-yl)-benzenesulfonamide as beige crystals; m.p. 240° C. (dec.).

EXAMPLE 7
4-Amino-N-(6-dimethylamino-2-methylamino-pyrimidin-4-yl)-benzenesulfonamide 0.314 g (0.001 mol) of 4-amino-N-(6-chloro-2-methylamino-pyrimidin-4-yl)-benzenesulfonamide and 18 ml (0.1 mol) of dimethylamine in ethanol (5.6M) were stirred in an autoclave at 130° C. for 4 hours. The reaction mixture was freed from solvent, the residue was suspended in 5 ml of ethanol and treated in an ultrasound bath for 15 min. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.30 g (78%) of 4-amino-N-(6-dimethylamino-2-methylamino-pyrimidin-4-yl)-benzenesulfonamide as beige crystals; m.p.: >300° C.

EXAMPLE 8
4-Amino-N-(6-azetidin-1-yl-2-methylamino-pyrimidin-4-yl)-benzenesulfonamide 0.314 g (0.001 mol) of 4-amino-N-(6-chloro-2-methylamino-pyrimidin-4-yl)-benzenesulfonamide and 1.0 ml (0.015 mol) of trimethyleneimine were stirred in 20 ml of ethanol in an autoclave at 130° C. for 4 hours. The reaction mixture was freed from solvent, the residue was suspended in 5 ml of ethanol and treated in an ultrasound bath for 15 mins. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.24 g (72%) of 4-amino-N-(6-azetidin-1-yl-2-methylamino-pyrimidin-4-yl)-benzenesulfonamide as white crystals; m.p.: 295–296° C.

EXAMPLE 9
4-Amino-N-(Z-methylamino-6-pyrrolidin-1-yl-pyrimidin-4-yl)-benzenesulfonamide 0.314 g (0.001 mol) of 4-amino-N-(6-chloro-2-methylamino-pyrimidin-4-yl)-benzenesulfonamide and 2.5 ml (0.15 mol) of pyrrolidine were stirred in 20 ml of ethanol in an autoclave at 130° C. for 4 hours. The reaction mixture was freed from solvent, the residue was suspended in 5 ml of ethanol and treated in an ultrasound bath for 15 min. The precipitate was filtered off, dissolved in 150 ml of 1N NaOH and filtered. The filtrate was adjusted to pH 6 with 1N HCl. The precipitate was filtered off under suction, washed with water and dried. There was obtained 0.22 g (63%) of 4-amino-N-(2-methylamino-6-pyrrolidin-1-yl-pyrimidin-4-yl)-benzenesulfonamide as beige crystals; m.p.: >300° C.

EXAMPLE 10
4-Amino-N-(2-ethylamino-6-methylamino-pyrimidin-4-yl)-benzenesulfonamide 2.0 g (0.011 mol) of (4,6-dichloropyrimidin-2-yl)-ethylamine and 5.67 g (0.022 mol) of N-(4-sulfamoyl-phenyl)-acetamide potassium salt were stirred in 10 ml of 1-methyl-2-pyrrolidone at 140° C. for 8 hours. Then, the solvent was distilled off in a high vacuum, the residue was partitioned in ethyl acetate/water, the inorganic phase was saturated with sodium chloride and the residual ethyl acetate dissolved in the aqueous phase was distilled off on a rotary evaporator. The aqueous phase was made acid with 1N HCl, the crystals which separated were filtered off under suction and washed with water. After drying there were obtained 2.88 g (75%) of N-[4-(6-chloro-2-ethylamino-pyrimidin-4-ylsulfamoyl)-phenyl]-acetamide as beige crystals, which were used directly in the next step.

2.88 g (0.0075 mol) of N-[4-(6-chloro-2-ethylamino-pyrimidin-4-ylsulfamoyl)-phenyl]-acetamide were dissolved in 76 ml of 1N NaOH and boiled at reflux for 3 hours. The mixture was extracted with ethyl acetate, the aqueous phase was saturated with sodium chloride and the residual ethyl acetate was distilled on a rotary evaporator. Then, the aqueous phase was made acid with 3N HCl and the precipitate which separated was filtered off under suction. After drying there were obtained 2.2 g (90%) of 4-amino-N-(6-chloro-2-ethylamino-pyrimidin-4-yl)-benzenesulfonamide as white crystals; m.p.: 172–173° C.

0.1 g (0.00031 mol) of 4-amino-N-(6-chloro-2-ethylamino-pyrimidin-4-yl)-benzenesulfonamide was dissolved in 20 ml of ethanol and stirred with 0.6 ml (0.0043 mol) of trimethylamine and 0.1 g (0.0015 mol) of methylamine hydrochloride in an autoclave at 130° C. for 4 hours. The reaction mixture was freed from solvent, the residue was suspended in 5 ml of ethanol and treated in an ultrasound bath for 15 minutes. The precipitate was filtered off, dissolved in 150 ml of 1N NaOH and filtered. The filtrate was adjusted to pH 6 with 0.1N HCl. The precipitate was filtered off under suction, washed with water and dried. There was obtained 0.053 g (54%) of 4-amino-N-(2-ethylamino-6-methylamino-pyrimidin-4-yl)-benzenesulfonamide as beige crystals; m.p.: 261–263° C.

EXAMPLE 11
4-Amino-N-(2.6-bis-ethylamino-pyrimidin-4-yl)-benzenesulfonamide 1.50 g (0.00483 mol) of sulfadimethoxine were dissolved in 25 ml of ethanol, treated with 12.5 ml (0.193 mol) of cooled ethylamine and stirred in an autoclave at 180° C. for 24 hours. The mixture was cooled and freed completely from solvent. The residue was suspended in 150 ml of hot ethanol and filtered off under suction. There was obtained 0.79 g (40%) of 4-amino-N-(2,6-bis-ethylamino-4-yl)-benzenesulfonamide as pale beige crystals; m.p. 245–250° C.

0.79 g (0.00234 mol) of 4-amino-N-(2,6-bis-ethylamino-pyrimidin-4-yl)-benzenesulfonamide was dissolved in 150 ml of methanol, treated with 2.0 ml (0.0070 mol) of 3.5N ethanolic hydrochloric acid and stirred at 0° C. for 2 hours. The solution was freed completely from solvent and the residue was recrystallized from ethanol/diethyl ether. There was obtained 0.61 g (70%) of 4-amino-N-(2,6-bis-ethylamino-pyrimidin-4-yl)-benzenesulfonamide hydrochloride as pale beige crystals; m.p. 197–208° C.

EXAMPLE 12
4-Amino-N-(2-ethylamino-6-isopropylamino-pyrimidin-4-yl)-benzenesulfonamide 0.5 g (0.0015 mol) of 4-amino-N-(6-chloro-2-ethylamino-pyrimidin-4-yl)-benzenesulfonamide was dissolved in 20 ml of ethanol and stirred with 13 ml (0.15 mol) of isopropylamine in an autoclave at 130° C. for 4 hours. The reaction mixture was freed from solvent, the residue was suspended in 5 ml of ethanol and treated in an ultrasound bath for 15 minutes. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.20 g (37%) of 4-amino-N-(2-ethylamino-6-isopropylamino-pyrimidin-4-yl)-benzenesulfonamide as white crystals; m.p.: 258–259° C.

EXAMPLE 13
4-Amino-N-(6-dimethylamino-2-ethylamino-pyrimidin-4-yl)-benzenesulfonamide 0.5 g (0.0015 mol) of 4-amino-N-(6-chloro-2-ethylamino-pyrimidin-4-yl)-benzenesulfonamide was dissolved in 20 ml of 33% dimethylamine in ethanol and stirred in an autoclave at 130° C. for 4 hours. The reaction mixture was freed from solvent, the residue was suspended in 5 ml of ethanol and treated in an ultrasound bath for 15 minutes. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.426 g (83%) of 4-amino-N-(6-dimethylamino-2-ethylamino-pyrimidin-4-yl benzenesulfonamide as white crystals; m.p.: 301–302° C.

EXAMPLE 14
4-Amino-N-(6-azetidin-1-yl-2-ethylamino-pyrimidin-4-yl)-benzenesulfonamide 0.3 g (0.000915 mol) of 4-amino-N-(6-chlor0-2-ethylamino-pyrimidin-4-yl)-benzenesulfonamide was dissolved in 20 ml of ethanol, treated with 0.93 ml (0.0137 mol) of trimethyleneimine and stirred in an autoclave at 130° C. for 4 hours. The reaction mixture was freed from solvent, the residue was suspended in 5 ml of ethanol and treated in an ultrasound bath for 15 min. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.248 g (78%) of 4-amino-N-(6-azetidin-1-yl-2-ethylamino-pyrimidin-4-yl)-benzenesulfonamide as white crystals; m.p.: 292–293° C.

EXAMPLE 15
4-Amino-N-(2,6-bis-propylamino-pyrimidin-4-yl)-benzenesulfonamide 1.50 g (0.00483 mol) of sulfadimethoxine were suspended in 20 ml of ethanol, treated with 16 ml (0.193 mol) of propylamine and stirred in an autoclave at 140° C. for 65 hours. The mixture was cooled and, after 24 hours., the crystals which separated were filtered off under suction. There was obtained 0.75 g (50%) of 4-amino-N-(2,6-bis-propylamino-pyrimidin-4-yl)-benzenesulfonamide as pale beige crystals; m.p. 211–215° C.

0.75 g (0.00205 mol) of 4-amino-N-(2,6-bis-propylamino-pyrimidin-4-yl)-benzenesulfonamide was dissolved in 100 ml of methanol, treated with 1.5 ml (0.0062 mol) of 3.5N ethanolic hydrochloric acid and stirred at 0° C. for 2 hours. The solution was freed completely from solvent and the residue was recrystallized from ethanol/diethyl ether. There was obtained 0.86 g (82%) of 4-amino-N-(2,6-bis-propylamino-pyrimidin-4-yl)-benzenesulfonamide hydrochloride as beige crystals; m.p. 189–195° C.

EXAMPLE 16
4-Amino-N-(6-ethylamino-2-isopropylamino-pyrimidin-4-yl)-benzenesulfonamide 2.42 g (0.0117 mol) of (4,6-dichloropyrimidin-2-yl)-ethylamine and 5.0 g (0.020 mol) N-(4-sulfamoyl-phenyl)-acetamide potassium salt were stirred in 10 ml of 1-methyl-2-pyrrolidone at 140° C. for 8 hours. Then, the solvent was distilled off in a high vacuum, the residue was partitioned in ethyl acetate/water, the inorganic phase was saturated with sodium chloride and the residual ethyl acetate dissolved in the aqueous phase was distilled off on a rotary evaporator. The aqueous phase was made acid with 1N HCl, the precipitate which thereby separated was filtered off under suction and washed with water. This was used directly without drying in the next step.

The crude product obtained in the step described previously was dissolved in 100 ml of 1N NaOH and boiled at reflux for 3 hours. The mixture was extracted with ethyl acetate, the aqueous phase was saturated with sodium chloride and the residual ethyl acetate was distilled off on a rotary evaporator. Then, the aqueous phase was made acid 3N HCl and the precipitate which thereby separated was filtered under suction. After drying they were obtained 2.22 g (55% based on the (4,6-dichloropyrimidine-2-yl)-ethylamine used in the preceding step) of 4-amino-N-(6-chloro-2-isopropylamino-pyrimidin-4-yl)-benzenesulfonamide as white crystals; m.p.: 94–95° C.

0.1 g (0.000293 mol) of 4-amino-N-(6-chloro-2-isopropylamino-pyrimidin-4-yl)-benzenesulfonamide was dissolved in 20 ml of ethanol, treated with 1.93 ml (0.0293 mol) of ethylamine and stirred in an autoclave at 130° C. for 4 hours. The reaction mixture was freed from solvent, the residue was suspended in 5 ml of ethanol and treated in an ultrasound bath for 15 min. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.044 g (43%) of 4-amino-N-(6-ethylamino-2-isopropylamino-pyrimidin-4-yl)-benzenesulfonamide as white crystals; m.p.: 266–267° C.

EXAMPLE 17
4-Amino-N-(2-dimethylamino-6-methylamino-pyrimidin-4-yl)-benzenesulfonamide 0.50 g (0.00153 mol) of 4-amino-N-(2-dimethylamino-6-chloro-pyrimidin-4-yl)-benzenesulfonamide were dissolved in 20 ml (0.176 mol) of 8M methylamine in ethanol and stirred in an autoclave at 130° C. for 4 hours. The reaction mixture was freed from solvent and the residue was chromatographed on silica gel with methanol/dichloromethane 1:19. There was obtained 0.10 g (21%) of 4-amino-N-(2-dimethylamino-6-methylamino-pyrimidin-4-yl)-benzenesulfonamide as beige crystals; m.p: 253–254° C.

EXAMPLE 18
4-Amino-N-(2-dimethylamino-6-ethylamino-pyrimidin-4-yl)-benzenesulfonamide 0.2 g (0.00061 mol) of 4-amino-N-(6-chloro-2-dimethylamino-pyrimidin-4-yl)-benzenesulfonamide were dissolved in 20 ml of ethanol, treated with 4.2 ml (0.061 mol) of ethylamine and stirred in an autoclave at 130° C. for 4 hours. The reaction mixture was freed from solvent, the residue was suspended in 5 ml of ethanol and treated in an ultrasound bath for 15 minutes. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.082 g (40%) of 4-amino-N-(2-dimethylamino-6-ethylamino-pyrimidin-4-yl)-benzenesulfonamide as beige crystals; m.p.: 237–238° C.

EXAMPLE 19
4-Amino-N-(2,6-bis-methylamino-pyrimidin-4-yl)-N-methyl-benzenesulfonamide 0.65 g (0.0021 mol) of 4-amino-N-(2,6-bis-methylamino-pyrimidin-4-yl)-benzenesulfonamide was dissolved in a mixture of 100 ml of methanol and 400 ml of dimethylformamide and treated with 60 ml of a solution of diazomethane in diethyl ether. The mixture was stirred at room temperature for 30 minutes. The solvent was distilled off and the residue was chromatographed over 50 g of $SiO_2$ with 5% of methanol in methylene chloride as the eluent. There was obtained 0.24 g (35%) of 4-amino-N-(2,6-bis-methylamino-pyrimidin-4-yl)-N-methyl-benzenesulfonamide as a yellow solid; m.p.: 79–80° C.

EXAMPLE 20
4-Amino-N-(6-azetidin-1-yl-2-dimethylamino-pyrimidin-4-yl)-benzenesulfonamide 0.20 g (0.00061 mol) of 4-amino-N-(6-chloro-2-dimethylamino-pyrimidin-4-yl)-benzenesulfonamide was dissolved in 20 ml of ethanol, treated with 0.62 ml (0.0092 mol) of trimethyleneimine and stirred in an autoclave at 130° C. for 4 hours. The reaction mixture was freed from solvent, the residue was suspended in 5 ml of ethanol and treated in an ultrasound bath for 15 minutes. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.13 g (61%) of 4-amino-N-(6-azetidin-1-yl-2-dimethylamino-pyrimidin-4-yl)-benzenesulfonamide as beige crystals; m.p.: 239–240° C.

EXAMPLE 21
4-Amino-N-(2-azetidin-1-yl-6-methylamino-pyrimidin-4-yl)-benzenesulfonamide 2.0 ml (0.030 mol) of trimethyleneimine and 2.30 ml (0.020 mol) of 2,4,6-trichloropyrimidine were stirred in 50 ml of ethanol at room temperature for 3 hours. The solvent was distilled off, the residue was suspended in diethyl ether and washed with saturated NaHCO$_3$ solution. The organic phase was dried over MgSO$_4$, concentrated and the residue was chromatographed on silica gel with diethyl ether/hexane 1:5 to 2:1 (gradient elution). The first fraction (R$_f$: 0.39, diethyl ether/hexane 1:3) contained 0.67 g (16%) of 2-azetidin-1-yl-4,6-dichloro-pyrimidine as white crystals; m.p: 109° C. The second fraction contained 1.50 g (37%) of 2,4-dichloro-6-azetidin-1-ethyl-pyrimidine as white crystals; m.p.: 129–130° C.

0.65 g (0.0032 mol) of 2-azetidin-1-yl-4-6-dichloro-pyrimidine and 1.6 g (0.0064 mol) of N-(4-sulfamoyl-phenyl)-acetamide potassium salt were stirred in 10 ml of 1-methyl-2-pyrrolidone at 140° C. for 8 hours. Then, the solvent was distilled off in a high vacuum, the residue was partitioned in ethyl acetate/water, the inorganic phase was saturated with sodium chloride and the residual ethyl acetate dissolved in the aqueous phase was distilled off on a rotary evaporator. The aqueous phase was made acid with 1N HCl and the precipitate which separated was filtered off under suction and washed with water. This was used directly without drying in the next step.

The crude product obtained in the step previously described was dissolved in 50 ml of 1N NaOH and boiled at reflux for 2 hours.

The mixture was extracted with ethyl acetate, the aqueous phase was saturated with sodium chloride and the residual ethyl acetate was distilled off on a rotary evaporator. Then, the aqueous phase was made acid with 3N HCl and the precipitate which thereby separated was filtered off under suction. After drying there was obtained 0.66 g (60% based on the 2-azetidin-1-yl-4,6-dichloro-pyrimidine used in the preceding step) of 4-amino-N-(2-azetidin-1-yl-6-chloro-pyrimidin-4-yl)-benzenesulfonamide as beige crystals; m.p.: >203° C. (dec.).

0.20 g (0.00059 mol) of 4-amino-N-(2-azetidin-1-yl-6-chloro-pyrimidin-4-yl)-benzenesulfonamide was dissolved in 20 ml of ethanol, treated with 0.4 g (0.00588 mol) of methylamine hydrochloride and 2.28 ml (0.0176 mol) of triethylamine and stirred in an autoclave at 130° C. for 8 hours. The reaction mixture was freed from solvent and the residue was chromatographed on silica gel with methanol/dichloromethane 1:19. There was obtained 0.053 g (27%) of 4-amino-N-(2-azetidin-1-yl-6-methylamino-pyrimidin-4-yl)-benzenesulfonamide as light beige crystals; m.p.: >260° C. (dec.)

EXAMPLE 22

4-Amino-N-(2-azetidin-1-yl-6-ethylamino-pyrimidin-4-yl)-benzenesulfonamide 0.2 g (0.00061 mol) of 4-amino-N-(2-azetidin-1-yl-6-chloro-pyrimidin-4-yl)-benzenesulfonamide was dissolved in 20 ml of ethanol, treated with 3.9 ml (0.061 mol) of ethylamine and stirred in an autoclave at 130° C. for 12 hours. The reaction mixture was free from solvent, the residue was suspended in 5 ml of ethanol and treated in an ultrasound bath for 15 minutes. The precipitate was filtered off, dissolved in 10 ml of 0.1N NaOH and filtered. The filtrate was adjusted to pH 6 with 0.1N HCl. The precipitate was filtered off under suction, washed with water and dried. There was obtained 0.090 g (44%) of 4-amino-N-(2-azetidin-1-yl-6-ethylamino-pyrimidin-4-yl)-benzenesulfonamide as beige crystals; m.p.: 260–262° C.

EXAMPLE 23

4-Amino-N-(6-methylamino-2-pyrrolidin-1-yl-pyrimidin-4-yl)-benzenesulfonamide 0.58 g (0.00266 mol) of 4,6-dichloro-2-pyrrolidin-1-yl-pyrimidine and 1.36 g (0.00539 mol) of N-(4-sulfamoyl-phenyl)-acetamide potassium salt were stirred in 10 ml of 1-methyl-2-pyrrolidone at 140° C. for 8 hours. Then, the solvent was distilled off in a high vacuum, the residue was partitioned in ethyl acetate/water and extracted. The aqueous phase was made acid with 4N HCl and extracted with ethyl acetate. Both organic phases were combined and concentrated. The residue was recrystallized from a small amount of ethanol and the mother liquor was chromatographed over silica gel with cyclohexane/ethyl acetate 2:1 as the eluent. There was obtained a total of 0.62 g (66%) of N-[4-(6-chloro-2-pyrrolidin-1-yl-pyrimidin-4-ylsulfamoyl)-phenyl]-acetamide as whitish crystals; m.p. 229–233° C.

0.62 g (0.00175 mol) of N-[4-(6-chloro-2-pyrrolidin-1-yl-pyrimidin-4-ylsulfamoyl)-phenyl]-acetamide was dissolved in 20 ml of ethanol, treated with 1.36 g (0.0201 mol) of methylamine hydrochloride and 5.3 ml (0.038 mol) of triethylamine and stirred in an autoclave at 140° C. for 17 hours. The mixture was freed completely from solvent, the residue was partitioned in ethyl acetate/water and filtered off under suction. There was obtained 0.30 g (44%) of N-[4-(6-methylamino-2-pyrrolidin-1-yl-pyrimidin-4-ylsulfamoyl)-phenyl]-acetamide as beige crystals; m.p. 271–274° C.

0.30 g (0.00077 mol) of N-[4-(6-methylamino-2-pyrrolidin-1-yl-pyrimidin-4-ylsulfamoyl)-phenyl]-acetamide was boiled at reflux in 30 ml of 1N aqueous sodium hydroxide for 3 hours. The mixture was cooled and extracted with ethyl acetate. Crystals then separated from the aqueous phase and, after suction filtration, were chromatographed over silica gel with ethyl acetate/ethanol 9:1 as the eluent. There was obtained 0.082 g (30%) of 4-amino-N-(6-methylamino-2-pyrrolidin-1-yl-pyrimidin-4-yl)-benzenesulfonamide as beige crystals; m.p. 299–301° C.

EXAMPLE 24

4-Amino-N-(6-amino-2-mercapto-pyrimidin-4-yl)-benzenesulfonamide 1 g (0.0043 mol) of 4-acetamino-benzenesulfochloride was dissolved in 20 ml of pyridine and treated with 0.64 g (0.0045 mol) of 4,6-diamino-pyrimidine-2-thiol. The mixture was stirred at room temperature for 2 hours., poured into 30 ml of water, the precipitate was filtered off under suction and dissolved in 40 ml of 1N NaOH. The reaction mixture was boiled at reflux for 2 hours., filtered, the filtrate was treated with 1N HCl to pH 6 and the precipitate which separated was filtered off. This was washed well with water and dried. There was obtained 0.96 g (75%) of 4-amino-N-(6-amino-2-mercapto-pyrimidin-4-yl)-benzenesulfonamide as yellowish crystals; m.p.: 232–234° C.

EXAMPLE 25

4-Amino-N-(2-amino-6-methoxy-pyrimidin-4-yl)-benzenesulfonamide 0.27 g (0.0009 mol) of 4-amino-N-(2-amino-6-chloro-pyrimidin-4-yl)-benzenesulfonamide was dissolved in a solution of 0.23 g of sodium in 20 ml of methanol and stirred in an autoclave at 150° C. for 9 hours. The solvent was distilled off, the residue was added to water and the pH value was adjusted to 4–5 with 1N HCl. The precipitate which thereby separated was filtered off under suction, washed with water and dried. The crystals obtained were triturated in 20 ml of methanol, again filtered off and dried in a high vacuum. There was obtained 0.25 g (94%) of 4-amino-N-

(2-amino-6-methoxy-pyrimidin-4-yl)-benzenesulfonamide as beige crystals; m.p.: >250° C. (dec.).

EXAMPLE 26
4-Amino-N-(4.6-bis-methylamino-pyrimidin-2-yl)-benzenesulfonamide 0.25 g (0.0008 mol) of 4-amino-N-(4,6-dimethoxy-pyrimidin-2-yl)-benzenesulfonamide was dissolved in 20 ml of 8M methylamine in ethanol and stirred in an autoclave at 130° C. for 21 hours. Thereafter, the reaction mixture was concentrated, the residue was suspended in 5 ml of ethanol, treated in an ultrasound bath and the precipitate was filtered off. This was dissolved in 5 ml of 1N NaOH, the solution was filtered and the pH value was adjusted to 5 with 1N HCl. The precipitate which thereby separated was filtered off and dried. There was obtained 0.1 g (42%) of 4-amino-N-(4,6-bis-methylamino-pyrimidin-2-yl)-benzenesulfonamide as yellow crystals; m.p.: 262–263° C.

EXAMPLE 27
N-(2,6-Bis-methylamino-pyrimidin-4-yl)-4-chloro-benzenesulfonamide 0.39 g (0.0022 mol) of (4,6-dichloro-pyrimidin-2-yl)-methylamine and 1.0 g (0.0044 mol) of 4-chloro-benzenesulfonamide potassium salt were stirred in 10 ml of 1-methyl-2-pyrrolidone at 150° C. for 8 hours. Then, the solvent was distilled off in a high vacuum, the residue was partitioned in ethyl acetate/water and extracted. The aqueous phase was saturated with sodium chloride, evaporated briefly in a vacuum, made acid with 4N HCl and extracted with dichloromethane. The two extracts were combined and chromatographed over silica gel with cyclohexane/ethyl acetate 1:1 as the eluent. There was obtained 0.62 g (85%) of 4-chloro-N-(6-chloro-2-methylamino-pyrimidin-4-yl)-benzenesulfonamide as white crystals. m.p. 196–198° C.

0.62 g (0.0019 mol) of 4-chloro-N-(6-chloro-2-methylamino-pyrimidin-4-yl)-benzenesulfonamide was dissolved in 10 ml of ethanol, treated with 1.67 g (0.025 mol) of methylamine hydrochloride and 6.2 ml (0.044 mol) of triethylamine and stirred in an autoclave at 140° C. for 18 hours. The mixture was freed completely from solvent, the residue was partitioned in ethyl acetate/water and the insoluble constituents were filtered off under suction. The filter cake was recrystallized in methanol/diethyl ether. There was obtained 0.28 g (45%) of N-(2,6-bis-methylamino-pyrimidin-4-yl)-4-chloro-benzenesulfonamide as white crystals; m.p. 272–273° C.

EXAMPLE 28
N-(2,6-Bis-methylamino-pyrimidin-4-yl)-4-tert-butyl-benzenesulfonamide 0.39 g (0.0022 mol) of (4,6-dichloro-pyrimidin-2-yl) methylamine and 1.1 g (0.0044 mol) of 4-tert-butyl-benzenesulfonamide potassium salt were stirred in 10 ml of 1-methyl-2-pyrrolidone at 150° C. for 8 hours. Then, the solvent was distilled off in a high vacuum, the residue was partitioned in ethyl acetate/water and extracted. The aqueous phase was saturated with sodium chloride, de-gassed in a vacuum and made acid with 4N HCl, with a precipitate separating. The mixture was suction filtered, the extract and the solid were combined and chromatographed over silica gel with cyclohexane/ethyl acetate 2:1 as the eluent. The product was recrystallized from ethyl acetate/n-hexane. There was obtained 0.57 g (73%) of 4-tert-butyl-N-(6-chloro-2-methylamino-pyrimidin-4-yl)-benzenesulfonamide as white crystals; m.p.: 118–137° C. (dec.).

0.47 g (0.0013 mol) of 4-tert-butyl-N-(6-chloro-2-methylamino-pyrimidin-4-yl)-benzenesulfonamide was dissolved in 10 ml of ethanol, treated with 1.3 g (0.019 mol) of methylamine hydrochloride and 4.7 ml (0.034 mol) of triethylamine and stirred in an autoclave at 140° C. for 18 hours. The mixture was freed completely from solvent, the residue was partitioned in ethyl acetate/water and the insoluble constituents were filtered off under suction. The filtered cake was recrystallized in methanol/diethyl ether. There was obtained 0.15 g (33%) of N-(2,6-bis-methylamino-pyrimidin-4-yl)-4-tert-butyl-benzenesulfonamide as white crystals; m.p. 316–318° C.

EXAMPLE 29
N-(2,6-Bis-methylamino-pyrimidin-4-yl)-4-fluoro-benzenesulfonamide 0.46 g (0.0026 mol) of (4,6-dichloro-pyrimidin-2-yl)-methylamine and 1.1 g (0.0051 mol) of 4-fluoro-benzenesulfonamide potassium salt were stirred in 10 ml of 1-methyl-2-pyrrolidone in 150° C. for 8 hours. Then, the solvent was distilled off in a high vacuum, the residue was partitioned in ethyl acetate/water and extracted. The aqueous phase was saturated with sodium chloride, evaporated briefly in a vacuum and made acid with 4N HCl, with a precipitate separating. The mixture was suctioned filtered, the extract and the solid were combined and chromatographed over silica gel with cyclohexane/ethyl acetate 2:1 as the eluent. The product was recrystallized from ethyl acetate/n-hexane. There was obtained 0.46 g (56%) of N-(6-chloro-2-methylamino-pyrimidin-4-yl)-4-fluoro-benzenesulfonamide as white crystals; m.p. 121–123 C.

0.36 g (0.0011 mol) of N-(6-chloro-2-methylamino-pyrimidin-4-yl)-4-fluoro-benzenesulfonamide was dissolved in 10 ml of ethanol, treated with 1.2 g (0.018 mol) of methylamine hydrochloride and 4.0 ml (0.029 mol) of triethylamine and stirred in an autoclave at 140° C. for 17 hours. The mixture was freed completely from solvent, the residue was partitioned in ethyl acetate/water, the insoluble constituents were filtered off under suction and extracted. The extract and the solid were combined and recrystallized from methanol/diethyl ether. There was obtained 0.15 g (43%) of N-(2,6-bis-methylamino-pyrimidin-4-yl)-4-fluoro-benzenesulfonamide as white crystals; m.p. 261–263° C.

EXAMPLE 30
N-(2,6-Bis-methylamino-pyrimidin-4-yl)-benzenesulfonamide 5.38 g (0.0275 mol) of benzene-sulfonamide potassium salt and 2.45 g (0.0138 mol) of 2-methylamino-4,6-dichloro-pyrimidine were suspended in 22 ml of 1-methyl-2-pyrrolidone and stirred at 150° C. for 24 hours. The solvent was removed in a high vacuum and the residue was suspended in 250 ml of water. The mixture was extracted three times with 100 ml of ethyl acetate each time and the combined organic phases were washed with 200 ml of saturated $NaHCO_3$. The combined aqueous phases were made acid with 3N HCl and the precipitate which thereby separated was filtered off under suction. It was chromatographed on silica gel with dichloromethane/methanol 99:1→98:2. The yellowish crystals obtained after the chromatography were suspended in 70 ml of 1N NaOH, the suspension was filtered and the clear filtrate was adjusted to pH 3.5 with 1N HCl. The precipitate which thereby separated was isolated and dried. There were obtained 1.9 g (46%) of N-(2-methylamino-6-chloro-pyrimidin-4-yl)-benzenesulfonamide as colorless crystals; m.p.: 186–187° C.

0.25 g (0.00084 mol) of N-(2-methylamino-6-chloro-pyrimidin-4-yl)-benzenesulfonamide was dissolved in 20 ml of 2M methylamine in THF and stirred in an autoclave at 130° C. for 3 hours. The mixture was freed from solvent, the residue was dissolved in 25 ml of 2N NaOH, filtered and the pH value of the filtrate was adjusted to 6 with 1N HCl. The precipitate was filtered off under suction, dried and chromatographed on silica gel with dichloromethane/methanol 95:5. There was obtained 0.09 g (36%) of N-(2,6-bis-methylamino-pyrimidin-4-yl)-benzenesulfonamide as yellowish crystals; m.p.: >260° C. (dec).

EXAMPLE 31
N-(2,6-Bis-methylamino-pyrimidin-4-yl)-4-methyl-benzenesulfonamide 0.30 g (0.00097 mol) of N-(2,6-dimethoxy-pyrimidin-4-yl)-4-methyl-benzenesulfonamide was dissolved in 30 ml of 33 per cent ethanolic methylamine and stirred in an autoclave at 140° C. for 24 hours. The mixture was cooled and suction filtered. There was obtained 0.125 g (42%) of N-(2,6-bis-methylamino-pyrimidin-4-yl)-4-methyl-benzenesulfonamide as grey crystals; m.p. 270–272° C.

EXAMPLE 32
N-(2,6-Bis-methylamino-pyrimidin-4-yl)-3-chloro-benzenesulfonamide 0.24 g (0.00135 mol) of (4,6-dichloro-pyrimidin-2-yl)-methylamine and 0.62 g (0.0027 mol) of 3-chloro-benzenesulfonamide potassium salt were stirred in 10 ml of 1-methyl-2-pyrrolidone at 150° C. for 8 hours. Then, the solvent was distilled off in a high vacuum, the residue was partitioned in ethyl acetate/water and extracted. The aqueous phase was made acid with 4N HCl and extracted with dichloromethane. The residue was chromatographed over silica gel with cyclohexane/ethyl acetate 2:1 as the eluent. There was obtained 0.24 g (53%) of 3-chloro-N-(6-chloro-2-methylamino-pyrimidin-4-yl)-benzenesulfonamide as yellow crystals; m.p. 120–130° C. (dec.).

0.10 g (0.00030 mol) of 3-chloro-N-(6-chloro-2-methylamino-pyrimidin-4-yl)-benzenesulfonamide was dissolved in 5 ml of EtOH, treated with 0.27 g (0.004 mol) of methylamine hydrochloride and 1 ml (0.007 mol) of triethylamine and stirred in an autoclave at 145° C. for 17 hours. The entire reaction mixture was partitioned in ethyl acetate/water and extracted. The residue was recrystallized from MeOH. There was obtained 0.04 g (41%) of N-(2,6-bis-methylamino-pyrimidin-4-yl)-3-chloro-benzenesulfonamide as white crystals; m.p. 167–168° C.

EXAMPLE 33
N-(2,6-Bis-methylamino-pyrimidin-4-yl)-3-trifluoromethyl-benzenesulfonamide 0.27 g (0.00155 mol) of (4,6-dichloro-pyrimidin-2-yl)-methylamine and 0.82 g (0.0031 mol) of 3-trifluoromethyl-benzenesulfonamide potassium salt were stirred in 10 ml of 1-methyl-2-pyrrolidone at 150° C. for 8 hours. Then, the solvent was distilled off in a high vacuum, the residue was partitioned in ethyl acetate/water and extracted. The aqueous phase was made acid with 4N HCl and extracted with dichloromethane. The residue was chromatographed over silica gel with cyclohexane/ethyl acetate 2:1 as the eluent. There was obtained 0.26 g (69%) of N-(6-chloro-2-methylamino-pyrimidin-4-yl)-3-trifluoromethyl-benzenesulfonamide as white/beige crystals; m.p.: 190–193° C.

0.10 g (0.00027 mol) of N-(6-chloro-2-methylamino-pyrimidin-4-yl)-3-trifluoromethyl-benzenesulfonamide was dissolved in 5 ml of EtOH, treated with 0.27 g (0.004 mol) of methylamine hydrochloride and 1 ml (0.007 mol) of triethylamine and stirred in an autoclave at 145° C. for 17 hours. The entire reaction mixture was partitioned in ethyl acetate/water and extracted. The residue was recrystallized in MeOH. There was obtained 0.055 g (56%) of N-(2,6-bis-methylamino-pyrimidin-4-yl)-3-trifluoromethyl-benzenesulfonamide as white crystals; m.p. 234–235° C.

EXAMPLE 34
4-Amino-N-(3,5-diamino-phenyl)-benzenesulfonamide 0.105 g (0.00033 mol) of N-[4-(3,5-diamino-phenylsulfamoyl)-phenyl]-acetamide was dissolved in 6.5 ml of 1N NaOH and boiled at reflux for 15 hours. The reaction mixture was treated with 50 ml of saturated ammonium chloride solution and extracted twice with 100 ml of ethyl acetate each time. The combined organic phases were washed with saturated sodium chloride solution and dried over $MgSO_4$. After removal of the solvent the residue was chromatographed on aluminium oxide (neutral, activity 1), firstly with 5% and then 10% methanol in dichloromethane. There was obtained 0.05 g (55%) of 4-amino-N-(3,5-diamino-phenyl)benzenesulfonamide as a beige solid; m.p.: 188–190° C.

EXAMPLE 35
4-Amino-N-(3,5-bis-methylamino-phenyl)-benzenesulfonamide hydrochloride 0.24 g (0.001 mol) of N-(3-acetylamino-5-nitro-phenyl)-acetamide was suspended in 20 ml of THF, treated with 0.092 g (0.0023 mol) of NaH and 10 ml of DMF and stirred at room temperature for 15 hours. Then, 0.29 ml (0.0046 mol) of methyl iodide was added thereto and the mixture was stirred for a further 48 hours. Subsequently, the solvent was distilled off, the residue was taken up in 100 ml of water, extracted four times with 80 ml of ethyl acetate each time, the combined organic phases were washed with saturated sodium chloride solution and dried over sodium sulfate. After removal of the solvent the residue was chromatographed on silica gel with 3% methanol in dichloromethane. There was obtained 0.2 g (75%) of N-[3-(acetyl-methyl-amino)-5-nitro-phenyl]-N-methyl-acetamide as a brown oil. MS (EI): m/e=265 ($C_{12}H_{15}N_3O_4^+$).

0.19 g (0.00072 mol) of N-[3-(acetyl-methyl-amino)-5-nitro-phenyl]-N-methyl-acetamide was dissolved in 15 ml of ethanol, treated with 0.019 g of Pd/C (10%) and hydrogenated with hydrogen gas at room temperature for 2 hours. The catalyst was filtered off, the solvent was distilled off and the residue was chromatographed on silica gel with ethyl acetate. There was obtained 0.16 g (94%) of N-[3-(acetyl-methyl-amino)-5-amino-phenyl]-N-methyl-acetamide as white crystals; m.p.: 179–181° C.

0.15 g (0.00063 mol) of N-[3-(acetyl-methyl-amino)-5-amino-phenyl]-N-methyl-acetamide was dissolved in 3 ml of pyridine, treated with 0.154 g (0.00064 mol) of 4-acetamino-benzenesulfochloride and stirred at room temperature for 16 hours. Subsequently, the mixture was freed from solvent, the residue was taken up in 25 ml of water, extracted four times with 200 ml of ethyl acetate each time and the combined organic phases were washed with saturated sodium chloride solution and dried over sodium sulfate. After removal of the solvent the residue was chromatographed on silica gel, firstly with 2% and then 5% methanol in dichloromethane. There was obtained 0.15 g (55%) of N-[3-(4-acetylamino-phenylsulfonylamino)-5-(acetyl-methyl-amino)-phenyl]-N-methyl-acetamide as an orange colored, amorphous solid. MS (ISN): m/e=431 ($C_{20}H_{23}N_4O_5S^-$).

0.113 g (0.00026 mol) of N-[3-(4-acetylamino-phenyl-sulfonylamino)-5-(acetyl-methyl-amino)-phenyl]-N-methyl-acetamide was dissolved in 10 ml of 1N NaOH and boiled at reflux for 2 hours. The mixture was neutralized with 1N HCl, extracted with ethyl acetate and the organic phase was dried over sodium sulfate. After removal of the solvent the residue was dissolved in 4 ml of methanol and treated with 3 ml of 2M HCl. After the addition of 7–8 ml of ethyl acetate the product separated out slowly. It was filtered off and dried in a vacuum. There was obtained 0.085 g (74%) of 4-amino-N-(3,5-bis-methylamino-phenyl)-benzenesulfonamide hydrochloride (1:2.6) as a pink coloured amorphous solid. MS (ISN): me/e=305 ($C_{14}H_{17}N_4O_2S^-$).

EXAMPLE 36
4-Amino-N-(3-methylamino-phenyl)-benzenesulfonamide 1.3 g (0.0079 mol) of N-(3-amino-phenyl)-benzenesulfonamide were dissolved in 50 ml of pyridine, treated with 1.94 g (0.0083 mol) of 4-acetamino-benzenesulfochloride and stirred at room temperature for 18 hours. The pyridine was distilled off, the residue was suspended in water and filtered under suction. The material on the suction filter was washed well with water and dried in a high vacuum. There were obtained 2.7 g (94%) of N-[4-[3-(acetyl-methyl-amino)-phenylsulfamoyl]-phenyl]-acetamide as a light yellow colored solid; m.p.: 258–260° C.

2.5 g (0.0069 mol) of N-[4-[3-(acetyl-methyl-amino)-phenylsulfamoyl]-phenyl]-acetamide were dissolved in 150 ml of 1N NaOH and boiled in reflux for 4 hours. Subsequently, the pH value was adjusted to 4 with 1N HCl and the precipitate which separated was filtered off. After drying the material on the suction filter was chromatographed on silica gel with 3% methanol with dichloromethane. There were obtained 1.64 g (85%) of 4-amino-N-(3-methylamino-phenyl)-benzenesulfonamide as a yellowish solid; m.p.: 134–135° C.

EXAMPLE 37
N-(3,5-Dimethoxy-phenyl)-3-trifluoromethyl-benzenesulfonamide 0.31 g (0.002 mol) of 3,5-dimethoxyaniline was dissolved in 10 ml of pyridine, treated with 0.54 g (0.0022 mol) of 3-trifluoromethyl-benzenesulfochloride and stirred for 2 hours. at room temperature. After removal of the solvent the residue was taken up in water, extracted with ethyl acetate, the organic phase was washed with saturated sodium chloride solution and dried over sodium sulfate. The solvent was evaporated and the residue was chromatographed on silica gel with hexane/ethyl acetate 2:1. There was obtained 0.68 g (94%) of N-(3,5-dimethoxy-phenyl)-3-trifluoromethyl-benzenesulfonamide as white crystals; m.p.: 78–81° C.

EXAMPLE 38
4-Amino-N-(2,6-dibromo-pyridin-4-yl)-benzenesulfonamide 5.1 g (0.02 mol) of 4-amino-2,6-dibromo-pyridine were dissolved in 100 ml of pyridine, treated with 7.1 g (0.03 mol) of 4-acetamino-benzenesulfochloride and stirred at 60° C. for 16 hours. After removal of the solvent the residue was taken up in 100 ml of 1N HCl, extracted twice with 100 ml of ethyl acetate each time, the combined organic phases were washed with saturated sodium chloride solution and dried over sodium sulfate. Then, the mixture was freed from solvent and the residue was dried in a high vacuum. There were obtained 7.2 g (79%) of N-[4-(2,6-dibromo-pyridin-4-ylsulfamoyl)-phenyl]-acetamide as yellow crystals; m.p.: >260° C. (dec.).

6.2 g (0.0138 mol) of N-[4-(2,6-dibromo-pyridin-4-yl-sulfamoyl)-phenyl]-acetamide were dissolved in 138 ml of 1N NaOH and boiled at reflux for 2 hours. After cooling the mixture was adjusted to pH 6 with 2N HCl and the precipitate which separated was filtered off. The material on the suction filter was washed well with water and dried. It was subsequently chromatographed on silica gel with ethyl acetate/hexane 1:2→1:1. There were obtained 4.86 g (86%) of 4-amino-N-(2,6-dibromo-pyridin-4-yl)-benzenesulfonamide as beige crystals; m.p.: 220–222° C.

EXAMPLE 39
4-Amino-N-(2-chloro-6-methylamino-pyridin-4-yl)-benzenesulfonamide dihydrochloride 0.82 g (0.005 mol) of 4-amino-2,6-dichloro-pyridine was dissolved in 25 ml of pyridine, treated with 1.3 g (0.0055 mol) of 4-acetamino-benzenesulfochloride and stirred at 60° C. for 16 hours. After removal of the solvent the residue was taken up in 50 ml of 1N HCl, extracted twice with 50 ml of ethyl acetate each time, the combined organic phases were washed with saturated sodium chloride solution and dried over sodium sulfate. Then, the mixture was freed from solvent and the residue was chromatographed on silica gel with ethyl acetate/hexane 4:1. There were obtained 1.45 g (80%) of N-[4-(2,6-dichloro-pyridin-4-ylsulfamoyl)-phenyl]-acetamide as yellow crystals; m.p.: >246° C. (dec.).

1.25 g (0.0035 mol) of N-[4-(2,6-dichloro-pyridin-4-yl-sulfamoyl)-phenyl]-acetamide were dissolved in 35 ml of 1N NaOH and boiled at reflux for 2 hours. After cooling the mixture was adjusted to pH 6 with 2N HCl and the precipitate which separated was filtered off. The material on the suction filter was washed well with water and dried. It was subsequently chromatographed on silica gel with ethyl acetate/hexane 1:2→1:1. There were obtained 1.04 g (93%) of 4-amino-N-(2,6-dichloro-pyridin-4-yl)-benzenesulfonamide as white crystals; m.p.: 209–211° C. (dec.).

0.11 g (0.00035 mol) of 4-amino-N-(2,6-dichloro-pyridin-4-yl)-benzenesulfonamide was stirred in 25 ml of liquid methylamine in an autoclave at 130° C. for 72 hours. After removal of the methylamine the residue was taken up in 5 ml of dichloromethane/methanol 1:1, filtered and, after removal of the solvent, chromatographed on silica gel with hexane/ethyl acetate 3:1, 2:1 and finally 1:1. The product, obtained as a white, amorphous solid substance, was dissolved in 2 ml of methanol, treated with 2 ml of 2N HCl/methanol, diluted with 20 ml of diethyl ether and filtered off under suction. The material on the suction filter was washed well with diethyl ether and dried in a high vacuum. There was obtained 0.055 g (41%) of 4-amino-N-(2-chloro-6-methylamino-pyridin-4-yl)-benzenesulfonamide dihydrochloride (1:2) as white crystals; m.p.: >215° C. (dec.).

EXAMPLE 40
4-Amino-N-( 2-bromo-6-methylamino-pyridin-4-yl)-benzenesulfonamide hydrochloride 0.81 g (0.002 mol) of 4-amino-N-(2,6-dibromo-pyridin-4-yl)-benzenesulfonamide was stirred in 35 ml of liquid methylamine in an autoclave at 130° C. for 44 hours. The methylamine was left to evaporate, the residue was dissolved in ethanol, treated with 2 g of silica gel, concentrated and the residue was chromatographed on silica gel, firstly with ethyl acetate/hexane 1:2, then with pure ethyl acetate. There was obtained 0.63 g (88%) of 4-amino-N-(2-bromo-6-methylamino-pyridin-4-yl)-benzenesulfonamide as a beige foam. 0.33 g (0.00092 mol) of this was dissolved in 10 ml of methanol, treated with 5 ml of 2M HCl in methanol, concentrated and again treated with 4 ml of methanol. The precipitate obtained was filtered off under suction, rinsed with a small amount of methanol and dried in a high vacuum. There was obtained 0.27 g (69%) of 4-amino-N-(2-bromo-6-methylamino-pyridin-4-yl)- benzenesulfonamide hydrochloride as white crystals; m.p.: 226–228° C. (dec.).

EXAMPLE 41

4-Amino-N-(2-bromo-6-ethylamino-pyridin-4-yl)-benzenesulfonamide 5.1 g (0.0125 mol) of 4-amino-N-(2,6-dibromo-pyridin-4-yl)-benzenesulfonamide were stirred in 100 ml of liquid ethylamine in an autoclave at 150° C. for 24 hours. The ethylamine was left to evaporate, the residue was dissolved in ethanol, treated with 5 g of silica gel, concentrated and the residue was chromatographed on silica gel, firstly with ethyl acetate/hexane 1:2 and then 1:1. There were obtained 2.15 g of a brown oil which was suspended in 200 ml of 25% HCl. The mixture was suction filtered, the filtrate was adjusted to pH 8 with 2N NaOH and the precipitate which separated was isolated. After drying in a high vacuum there was obtained 0.96 g (21%) of 4-amino-N-(2-bromo-6-ethylamino-pyridin-4-yl)-benzenesulfonamide as beige crystals; m.p.: >85° C. (dec.).

EXAMPLE 42

4-Amino-N-(2,6-bis-methylamino-pyridin-4-yl)-benzenesulfonamide hydrochloride 0.90 g (0.002 mol) of 4-amino-N-(2,6-dibromo-pyridin-4-yl)-benzenesulfonamide was stirred in 35 ml of liquid methylamine in an autoclave at 160° C. for 16 hours. The methylamine was left to evaporate, the residue was dissolved in ethanol, treated with 1 g of silica gel, concentrated and the residue was chromatographed on silica gel, firstly with ethyl acetate/hexane 1:1 and then with pure ethyl acetate. There was obtained 0.34 g of a brown oil which was suspended in 100 ml of 1N NaOH. The mixture was suction filtered, the filtrate was adjusted to pH 8 with 1N HCl and the precipitate which separated was isolated. After drying with a high vacuum there was obtained 0.22 g (35%) of 4-amino-N-(2,6-bis-methylamino-pyridin-4-yl)-benzenesulfonamide hydrochloride (1:3) as beige crystals; m.p.: >280° C. (dec.). These were dissolved in 5 ml of methanol and treated with 3 ml of 2N methanolic HCl. The precipitate which separated was filtered off and dried. There was obtained 0.13 g of 4-amino-N-(2,6-bis-methylamino-pyridin-4-yl)-benzenesulfonamide hydrochloride (1:3) as light beige crystals; m.p.: 197° C. (dec.).

EXAMPLE 43

4-Amino-N-(2-ethylamino-6-methylamino-pyridin-4-yl)-benzenesulfonamide 2.5 g (0.007 mol) of 4-amino-N-(2-bromo-6-methylamino-pyridin-4-yl)-benzenesulfonamide were stirred with 80 ml of ethylamine in an autoclave at 160° C. for 40 hours. The residual ethylamine was left to evaporate and the residue was chromatographed on silica gel with ethyl acetate/hexane 1:2, then 2:3 and finally 1:1. The thus-obtained 0.67 g of brown oil was suspended in 200 ml of 1N NaOH, suction filtered and the filtrate was neutralized with 1N HCl. It was again suction filtered, the filtrate was saturated with NaCl and extracted with ethyl acetate. The organic phase was dried. There was obtained 0.055 g (2.5%) of 4-amino-N-(2-ethylamino-6-methylamino-pyridin-4-yl)-benzenesulfonamide as pale brown crystals; MS (ISN): me/e=320 ($C_{14}H_{18}N_5O_2S^-$).

EXAMPLE 44

4-Amino-N-(2-dimethylamino-6-methylamino-pyridin-4-yl)-benzenesulfonamide 2.5 g (0.007 mol) of 4-amino-N-(2-bromo-6-methylamino-pyridin-4-yl)-benzenesulfonamide were stirred with 80 ml of dimethylamine in an autoclave at 160° C. for 7 hours. The residual dimethylamine was left to evaporate and the residue was chromatographed on silica gel with ethyl acetate/hexane 1:1, then 2:1 and finally 3:1. The polar fractions were chromatographed twice on silica gel with ethyl acetate/hexane 2:3 and 1:1 as the eluent. There was obtained 0.175 g (8%) of 4-amino-N-(2-dimethylamino-6-methylamino-pyridin-4-yl)-benzenesulfonamide as beige crystals: MS (ISP): me/e=322 ($C_{14}H_{20}N_5O_2S^+$).

EXAMPLE 45

4-Amino-N-(2,6-bis-ethylamino-pyridin-4-yl)-benzenesulfonamide 5.1 g (0.0125 mol) of 4-amino-N-(2,6-dibromo-pyridin-4-yl)-benzenesulfonamide were stirred in 100 ml of liquid ethylamine in an autoclave at 150° C. for 24 hours. The ethylamine was left to evaporate, the residue was dissolved in ethanol, treated with 5 g of silica gel, concentrated and the residue was chromatographed on silica gel, firstly with ethyl acetate/hexane 1:2, then 1:1 and finally 2:1. There were obtained 1:16 g of a brown solid which was suspended in 500 ml of 1N NaOH. The mixture was filtered, the filtrate was adjusted to pH 8, again filtered and the filtrate was extracted with ethyl acetate. The filter material of the last filtration was combined with the ethyl acetate phase, concentrated and the residue was chromatographed on silica gel with ethyl acetate/hexane 2:1. There was obtained 0.22 g of a brown coloured solid which was suspended in 20 ml of 1N NaOH. The mixture was again filtered, the filtrate was adjusted to pH 8 with 1N HCl and the product which separated was filtered off under suction. There was obtained 0.14 g (3%) of 4-amino-N-(2,6-bis-ethylamino-pyridin-4-yl)-benzenesulfonamide as beige crystals; m.p.: 212–215° C. (dec.).

EXAMPLE 46

4-Amino-N-(2-methylamino-pyridin-4-yl)-benzenesulfonamide 0.5 g (0.0014 mol) of 4-amino-N-(2-bromo-6-methylamino-pyridin-4-yl)-benzenesulfonamide was dissolved in 25 ml of ethanol, treated with 0.05 g of Pd/C and hydrogenated with hydrogen gas under normal pressure for 1 hour. The catalyst was filtered off, the filtrate was concentrated and the residue was dissolved in 10 ml of 1N NaOH, filtered and the filtrate was then adjusted pH 8 by means of 1N HCl. The precipitate which separated slowly was filtered off under suction, rinsed and dried in a high vacuum. There was obtained 0.22 g (57%) of 4-amino-N-(2-methylamino-pyridin-4-yl)-benzenesulfonamide as white crystals; m.p.: >261° C. (dec).

EXAMPLE 47

4-Amino-N-(2.6-bis-dimethylamino-pyridin-4-yl)-benzenesulfonamide 0.81 g (0.002 mol) of 4-amino-N-(2,6-dibromo-pyridin-4-yl)-benzenesulfonamide was stirred in 30 ml of dimethylamine in an autoclave in 160° C. for 45 hours. The excess dimethylamine was left to evaporate, the residue was dissolved in a mixture of methanol and ethyl acetate, treated with 1 g of silica gel, concentrated and the residue was chromatographed on silica gel, firstly with ethyl acetate/hexane 1:3 and then 1:2. After drying in a high vacuum there was obtained 0.67 g (100%) of 4-amino-N-(2,6-bis-dimethylamino-pyridin-4-yl)-benzenesulfonamide as beige crystals; m.p.: 157–160° C. (dec.).

EXAMPLE 48
N-(2,6-Bis-methylamino-pyridin-4-yl)-4-chloro-benzenesulfonamide dihydrochloride 3.0 g (0.012 mol) of 4-amino-2,6-dibromo-pyridine were dissolved in 60 ml of pyridine, treated with 2.76 g (0.013 mol) of 4-chloro-benzenesulfochloride and stirred at 60° C. for 5 hours. After removal of the solvent the residue was taken up in 100 ml of 1N HCl, extracted twice with 100 ml of ethyl acetate each time, the combined organic phases were washed with saturated sodium chloride solution and dried over sodium sulfate. The mixture was freed from solvent and the residue was chromatographed on silica gel with ethyl acetate/hexane 1:4 and then 1:1. There were obtained 4.4 g (87%) of 4-chloro-N-(2,6-dibromo-pyridin-4-yl)-benzenesulfonamide as yellow crystals. For analytical purposes, 0.2 g (0.0005 mol) was recrystallized from tert-butyl methyl ether; m.p.: 203–205° C. (dec.).

0.50 g (0.0017 mol) of 4-chloro-N-(2,6-dibromo-pyridin-4-yl)-benzenesulfonamide was stirred in 35 ml of liquid methylamine with 0.025 g of Cu powder in an autoclave at 80° C. for 18 hours. The methylamine was left to evaporate, the residue was dissolved in 50 ml of water, the pH value was adjusted to 8 and the mixture was extracted three times with 100 ml of ethyl acetate each time. The combined organic phases were washed with saturated sodium chloride solution and dried over sodium sulfate. They were concentrated and the residue was suspended in 1N NaOH. After filtration the clear filtrate was saturated with NaCl and acidified to pH 1 with 1N HCl. A beige precipitate thereby separated and was isolated. There was obtained 0.24 g (50%) of N-(2,6-bis-methylamino-pyridin-4-yl)-4-chloro-benzenesulfonamide dihydrochloride as beige crystals; m.p.: >170° C. (dec).

EXAMPLE 49
3-Chloro-N-(2,6-bis-methylamino-pyridin-4-yl)-benzenesulfonamide 2.0 g (0.0079 mol) of 4-amino-2,6-dibromo-pyridine were dissolved in 24 ml of pyridine, treated with 2.5 g (0.012 mol) of 3-chloro-benzenesulfochloride and stirred at 60° C. for 5 hours. After removal of the solvent the residue was taken up in 100 ml of 1N HCl, extracted twice with 100 ml of ethyl acetate each time, the combined organic phases were washed with saturated sodium chloride solution and dried over sodium sulfate. The mixture was freed from solvent and the residue was chromatographed on silica gel with ethyl acetate/hexane 1:2, then 1:1 and finally 2:1. There were obtained 2.12 g (63%) of 3-chloro-N-(2,6-dibromo-pyridin-4-yl)-benzenesulfonamide as yellow crystals; m.p.: 187–189° C.

1.0 g (0.0023 mol) of 3-chloro-N-(2,6-dibromo-pyridin-4-yl)-benzenesulfonamide was stirred in 35 ml of liquid methylamine in an autoclave at 160° C. for 18 hours. The methylamine was left to evaporate, the residue was dissolved in water, the pH value was adjusted to 8 and the mixture was extracted three times with 100 ml of ethyl acetate each time. The combined organic phases were washed with saturated sodium chloride solution and dried over sodium sulfate. The solvent was evaporated and the residue was chromatographed on silica gel, firstly with ethyl acetate/hexane 2:1, then with pure ethyl acetate and finally with ethyl acetate/methanol 1:1. Subsequently, the product fraction was again chromatographed on silica gel with hexane/ethyl acetate 1:1. There was obtained 0.165 g (22%) of 3-chloro-N-(2,6-bis-methylamino-pyridin-4-yl)-benzenesulfonamide as light reddish coloured crystals. 0.13 g (0.0004 mol) of these were suspended in 20 ml of 1N NaOH, filtered and the clear filtrate was adjusted to pH 8 with 1N HCl. The precipitate which thereby separated was filtered off under suction and dried in a high vacuum. There was obtained 0.11 g (15%) of 3-chloro-N-(2,6-bis-methylamino-pyridin-4-yl)-benzenesulfonamide; m.p.: 133° C. (dec.).

EXAMPLE 50
N-(2,6-Bis-methylamino-pyridin-4-yl)-3-trifluoromethyl-benzenesulfonamide dihydrochloride 3.0 g (0.0012 mol) of 4-amino-2,6-dibromo-pyridine were dissolved in 60 ml of pyridine, treated with 2.1 ml (0.013 mol) of 3-trifluoromethyl-benzenesulfochloride and stirred at 60° C. for 5 hours. After removal of the solvent the residue was taken up in 100 ml of water, extracted twice with 100 ml of diethyl ether each time, the combined organic phases were washed with saturated sodium chloride solution and dried over sodium sulfate. The mixture was freed from solvent and the residue was chromatographed on silica gel with ethyl acetate/hexane 1:2 and then 1:1. There were obtained 4.77 g (87%) of N-(2,6-dibromo-pyridin-4-yl)-3-trifluoromethyl-benzenesulfonamide as pale yellow crystals. By crystallization in tert-butyl methyl ether there was obtained an analytically pure sample; m.p. 149–151° C.

0.50 g (0.0011 mol) of N-(2,6-dibromo-pyridin-4-yl)-3-trifluoromethyl-benzenesulfonamide was stirred in 35 ml of liquid methylamine with 0.022 g of Cu powder in an autoclave at 80° C. for 18 hours. The methylamine was left to evaporate, the residue was dissolved in 50 ml of water, the pH value was adjusted 8 with 1N HCl and the mixture was extracted three times with 100 ml of ethyl acetate each time. The combined organic phases were washed with saturated sodium chloride solution and dried over sodium sulfate. The mixture was concentrated and the residue was chromatographed on silica gel with ethyl acetate/hexane 1:9, 1:4, 1:1 and 1:0. The fraction obtained with pure ethyl acetate was suspended in 1N NaOH. After filtration the clear filtrate was saturated with NaCl and acidified to pH 1 with 1N HCl. A beige precipitate thereby separated and was isolated. There was obtained 0.094 g (15%) of N-(2,6-bis-methylamino-pyridin-4-yl)-3-trifluoromethyl-benzenesulfonamide dihydrochloride as beige crystals; m.p.: >227° C. (dec.).

EXAMPLE 51
4-Amino-N-(2-methyl-6-methylamino-pyridin-4-yl)-benzenesulfonamide 1.54 g (0.0082 mol) of 4-amino-2-bromo-6-methyl-pyridine were dissolved in 25 ml of pyridine, treated with 2.9 g (0.0124 mol) of 4-acetamino-benzenesulfochloride and stirred at 60° C. for 16 hours. After removal of the solvent the residue was chromatographed on silica gel with ethyl acetate as the eluent. The product-containing fractions were freed from solvent and dried in a high vacuum. There were obtained 2.17 g (69%) of N-[4-(2-bromo-6-methyl-pyridin-4-ylsulfamoyl)-phenyl]-acetamide as colourless crystals; m.p.: 262–264° C. (dec.).

1.15 g (0.003 mol) of N-[4-(2-bromo-6-methyl-pyridin-4-ylsulfamoyl)-phenyl]-acetamide were dissolved in 15 ml of 2N NaOH and boiled at reflux for 1 hour. After cooling the mixture was acidified to pH 5 with 2N HCl and the colourless precipitate which separated was filtered off. The material on the suction filter was washed with copious water and dried. There was obtained 0.95 g (93%) of 4-amino-N-(2-bromo-6-methyl-pyridin-4-yl)-benzenesulfonamide as colorless crystals; m.p.: >110° C. (dec.).

0.94 g (0.00275 mol) of 4-amino-N-(2-bromo-6-methyl-pyridin-4-yl)-benzenesulfonamide was stirred in 50 ml of 8M methylamine in ethanol in an autoclave at 135° C. for 40 hours. The methylamine was allowed to evaporate, the residue was dissolved in ethanol, treated with 2 g of silica gel, concentrated and the residue was chromatographed on silica gel, firstly with ethyl acetate/hexane 1:1, then 9:1. There was obtained 0.39 g (48%) of 4-amino-N-(2-methyl-6-methylamino-pyridin-4-yl)-benzenesulfonamide as colourless crystals; m.p.: 173–175° C. 0.081 g (0.00028 mol) thereof was recrystallized from methanol, diethyl ether and hexane, dried in a high vacuum, dissolved in 3 ml of methanol and treated with 2.8 ml of 0.1N NaOH. The methanol was distilled off and the residue was freeze-dried twice. There was obtained 0.084 g (97%) of 4-amino-N-(2-methyl-6-methylamino-pyridin-4-yl)-benzenesulfonamide sodium salt (1:1) as white crystals; MS (ISP): me/e=293 ($C_{13}H_{17}N_4O_2S^+$). 0.31 g (0.0011 mol) of 4-amino-N-(2-methyl-6-methylamino-pyridin-4-yl)-benzenesulfonamide was dissolved in 2 ml of methanol, treated with 1 ml of 2.4N HCl in diethyl ether and freed from solvent. The residue was dissolved in 1 ml of methanol and slowly added dropwise to diethyl ether while stirring-vigorously. A colourless precipitate thereby separated and this was isolated and dried in a high vacuum. There was obtained 0.33 g (87%) of 4-amino-N-(2-methyl-6-methylamino-pyridin-4-yl)-benzenesulfonamide hydrochloride (1:1.86) as white crystals; m.p.: >170° C. (dec.).

EXAMPLE 52

4-Amino-N-(1H-indol-4-yl)-benzenesulfonamide 0.095 g (0.00072 mol) of 4-amino-1H-indole was dissolved in 3 ml of pyridine, treated with 0.20 g (0.00086 mol) of 4-acetamino-benzenesulfochloride and stirred at 60° C. for 16 hours. After removal of the solvent the residue was taken up in 10 ml of 1N HCl, extracted twice with 20 ml of ethyl acetate each time, the combined organic phases were washed with saturated sodium chloride solution and dried over sodium sulfate. Then, the mixture was freed from solvent and the residue was dried in a high vacuum. There was obtained 0.155 g (65%) of N-[4-(1H-indol-4-ylsulfamoyl)-phenyl]-acetamide as pale grey crystals; m.p.: >260° C.

0.15 g (0.00045 mol) of N-[4-(1H-indol-4-ylsulpjamoyl)-phenyl]-acetamide was dissolved in 4 ml of 1N NaOH and boiled at reflux for 1 hour. After cooling the mixture was adjusted to pH 6 with 0.1N HCl and the precipitate which separated was filtered off. The material on the suction filter was washed with copious water and dried. It was subsequently chromatographed on silica gel with ethyl acetate/hexane 1:1. There was obtained 0.085 g (66%) of 4-amino-N-(1H-indol-4-yl)-benzenesulfonamide as a white amorphous solid; m.p.: 215° C.

EXAMPLE 53

4-Amino-N-(2-methylamino-6-trifluoromethyl-pyridin-4-yl)-benzenesulfonamide 0.15 g (0.00076 mol) of 4-amino-2-chloro-6-trifluoromethylpyridine was dissolved in 4 ml of pyridine, treated with 0.26 g (0.0015 mol) of 4-acetamino-benzenesulfochloride and stirred at 60° C. for 20 hours. After removal of the solvent the residue was taken up in 10 ml of 1N HCl, extracted twice with 20 ml of ethyl acetate each time, the combined organic phases were washed with saturated sodium chloride solution and dried over sodium sulfate. Then, the mixture was freed from solvent and the residue was dried in a high vacuum. There was obtained 0.20 g (67%) of N-[4-(2-chloro-6-trifluoromethyl-pyridin-4-ylsulfamoyl)-phenyl]-acetamide as orange-yellow crystals; MS (ISP): me/e =394 ($C_{14}H_{12}ClF_3N_3O_3S^+$).

0.20 g (0.0005 mol) of N-[4-(2-chloro-6-trifluoromethyl-pyridin-4-ylsulfamoyl)-phenyl]-acetamide was dissolved in a mixture of 5 ml of 1N NaOH and 5 ml of dioxan and boiled at reflux for 5 hours. After cooling the dioxan was distilled off, the residue was adjusted to pH 6 with 0.1 N HCl, the aqueous phase was extracted with ethyl acetate, back-washed with saturated sodium chloride solution and the organic phase was dried over $Na_2SO_4$. Subsequently, chromatography was carried out on silica gel with ethyl acetate/hexane 1:4. There was obtained 0.06 g (34%) of 4-amino-N-(2-chloro-6-trifluoromethyl-pyridin-4-yl)-benzenesulfonamide as pale yellow crystals; m.p.: 179–181° C.

0.052 g (0.00015 mol) of 4-amino-N-(2-chloro-6-trifluoromethyl-pyridin-4-yl)-benzenesulfonamide was stirred in 30 ml of 8M methylamine in ethanol in an autoclave at 135° C. for 80 hours. The methylamine was allowed to evaporate, the residue was dissolved in ethanol, treated with 2 g of silica gel, concentrated and the residue was chromatographed on silica gel with ethyl acetate/hexane 1:2. There was obtained 0.036 g (70%) of 4-amino-N-(2-methylamino-6-trifluoromethyl-pyridin-4-yl)-benzenesulfonamide as colorless crystals; m.p.: >68° C. (dec.).

EXAMPLE A

Tablets of the following composition are produced in the usual manner:

|  | mg/tablet |
| --- | --- |
| Active substance | 100 |
| Powd. lactose | 95 |
| White corn starch | 35 |
| Polyvinylpyrrolidone | 8 |
| Na carboxymethylstarch | 10 |
| Magnesium stearate | 2 |
| Tablet weight | 250 |

We claim:

1. A compound of formula

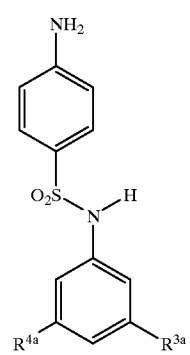

Ia$_1$ wherein $R^{3a}$ is halogen, amino or lower alkylamino; and $R^{4a}$ is amino or lower alkylamino, or a pharmaceutically acceptable salt thereof.

2. A compound according to claim 1, wherein $R^{3a}$ is amino or methylamino and $R^{4a}$ is amino or methylamino.

3. A compound according to claim 1, wherein $R^{3a}$ is amino and $R^{4a}$ is amino.

4. A compound according to claim 1, wherein $R^{3a}$ is methylamino and $R^{4a}$ is methylamino.

5. A compound of formula

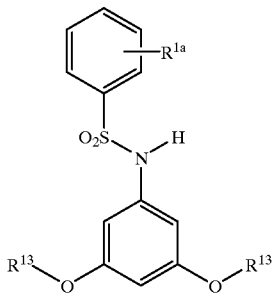

Ia₂ wherein
R¹ᵃ is 3-trifluoromethyl, 3-halo or 4-halo; and
R¹³ is lower alkyl,
or a pharmaceutically acceptable salt thereof.

6. A compound according to claim 5, wherein R¹ᵃ is 3-trifluoromethyl and R¹³ is methyl.

7. A pharmaceutical composition comprising a compound of formula

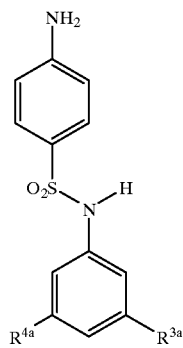

Ia₁ wherein
R³ᵃ is halogen, amino or lower alkylamino; and
R⁴ᵃ is amino or lower alkylamino
or a pharmaceutically acceptable salt thereof, and a pharmaceutically inert carrier.

8. A pharmaceutical composition according to claim 7, wherein R³ᵃ is amino or methylamino and R⁴ᵃ is amino or methylamino.

9. A pharmaceutical composition comprising a compound of formula

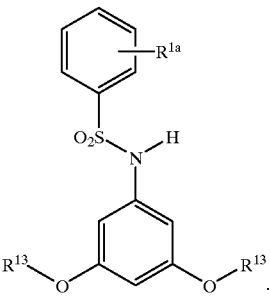

Ia₂ wherein
R¹ᵃ is 3-trifluoromethyl, 3-halo or 4-halo; and
R¹³ is lower alkyl,
or a pharmaceutically acceptable salt thereof, and a pharmaceutically inert carrier.

10. A pharmaceutical composition according to claim 9, wherein R¹ᵃ is trifluoromethyl and R¹³ is methyl.

* * * * *

UNITED STATES PATENT AND TRADEMARK OFFICE
CERTIFICATE OF CORRECTION

PATENT NO. : 5,998,665
DATED : December 7, 1999
INVENTOR(S) : Bös, et al.

It is certified that error appears in the above-identified patent and that said Letters Patent is hereby corrected as shown below:

Title Page:

--- [30] Foreign Application Priority     EP 96110462.7 – 6/28/96

EP 97105363.2 – 4/1/97 --- .

Signed and Sealed this

Twenty-fifth Day of July, 2000

Attest:

Q. TODD DICKINSON

*Attesting Officer*         *Director of Patents and Trademarks*